US008968811B2

(12) United States Patent
Lopez Mas et al.

(10) Patent No.: US 8,968,811 B2
(45) Date of Patent: *Mar. 3, 2015

(54) HYDROXYTROSOL CONTAINING EXTRACT OBTAINED FROM OLIVES AND SOLIDS CONTAINING RESIDUES OF OLIVE OIL EXTRACTION

(75) Inventors: Jose A. Lopez Mas, Murcia (ES); Sergio A. Streitenberger, Murcia (ES); Marcos Peñalver Mellado, Murcia (ES); Pedro Martinez Ortiz, Murcia (ES)

(73) Assignee: Probelte Pharma, S.A., Espinardo, Murcia (ES)

( * ) Notice: Subject to any disclaimer, the term of this patent is extended or adjusted under 35 U.S.C. 154(b) by 56 days.

This patent is subject to a terminal disclaimer.

(21) Appl. No.: 13/543,086

(22) Filed: Jul. 6, 2012

(65) Prior Publication Data
US 2013/0178537 A1 Jul. 11, 2013

Related U.S. Application Data

(63) Continuation-in-part of application No. 12/524,603, filed as application No. PCT/IB2008/000173 on Jan. 25, 2008, now Pat. No. 8,236,993.

(30) Foreign Application Priority Data

Jan. 26, 2007 (EP) .................................... 07001791
Jul. 23, 2007 (EP) .................................... 07014390

(51) Int. Cl.
| | | |
|---|---|---|
| A23L 1/00 | (2006.01) | |
| C07C 37/68 | (2006.01) | |
| A61K 31/05 | (2006.01) | |
| A61K 8/34 | (2006.01) | |
| A61Q 19/00 | (2006.01) | |
| A61K 8/97 | (2006.01) | |
| A23L 1/30 | (2006.01) | |
| A61K 36/63 | (2006.01) | |

(52) U.S. Cl.
CPC ................. *A61K 31/05* (2013.01); *A61K 8/347* (2013.01); *A61Q 19/00* (2013.01); *A61K 8/97* (2013.01); *A23L 1/3002* (2013.01); *A61K 36/63* (2013.01); *A61K 2800/10* (2013.01); *A23V 2002/00* (2013.01); *A61K 2236/39* (2013.01)
USPC ............ 426/431; 426/429; 568/750; 568/753

(58) Field of Classification Search
None
See application file for complete search history.

(56) References Cited

U.S. PATENT DOCUMENTS

| | | |
|---|---|---|
| 6,361,803 B1 | 3/2002 | Cuomo et al. |
| 6,849,770 B2 | 2/2005 | Guzmann et al. |
| 6,942,890 B1 | 9/2005 | van Buuren et al. |
| 2004/0102657 A1 | 5/2004 | Fernandez-Bolanos Guzman |
| 2004/0176647 A1 | 9/2004 | Perdices et al. |

FOREIGN PATENT DOCUMENTS

| | | |
|---|---|---|
| EP | 1 582 512 A1 | 10/2005 |
| EP | 1 623 960 A1 | 2/2006 |
| WO | WO 2004/005228 A1 | 1/2004 |

OTHER PUBLICATIONS

Frank et al., "Characterization of an Intense Bitter-Tasting 1 H, 4 H-Quinolizinium-7-olate by Appliation of the Taste Dilution Analysis, a Novel Bioassay for the Screening and Identification of Taste-Active Compounds in Foods," J. Agric. Food Chem. 2001, 49, 231-238.
Mateos et al., "Evaluation of Virgin Olive Oil Bitterness by Quantification of Secoridoid Derivatives," JAOCS, vol. 81, No. 1 (2004), 71-75.
Andrewes et al., "Sensory Properties of Virgin Olive Oil Polyphenols: Identification of Deacetoxy-ligstroside Aglycon as a Key Contributor to Pungency," J. Agric. Food Chem. 2003, 51, 1415-1420.
Beauchamp et al., "Ibuprofen-like activity in extra-virgin olive oil," Nature, vol. 437, Sep. 2005, 45-46.
Gutierrez-Rosales et al., "Main Polyphenols in the Bitter Taste of Virgin Olive Oil. Structural Confirmation by On-Line High-Performance Liquid Chromatography Electrospray Ionization Mass Spectrometry," J. Agric. Food Chem. 2003, 51, 6021-6025.
Database CAPLUS on STN, Acc. No. 2004:143424, Fernandez-Bolanos Guzmann, ES 2172429 A1 (Sep. 16, 2002) (abstract).
International Search Report for PCT International Application No. PCT/IB2008/000173 mailed May 23, 2008.

*Primary Examiner* — Brian J Davis
(74) *Attorney, Agent, or Firm* — RatnerPrestia

(57) ABSTRACT

Hydroxytyrosol extracted from olives and/or from the solid residues of olives after the extraction of olive oil, by acid hydrolysis and purification on resin columns eluted with water contains hydroxytyrosol and tyrosol, is free from sugars, has a residual content of Benzo[a]pyrene that is less than 2 microg/Kg (weight BaP/weight of extract as dry matter), containing a weight ratio of hydroxytyrosol to hydroxymethylfurfural of between 45:1 and 10000:1, and the content of hydroxytyrosol in the extract is at least 0.5% (w/w) with purity of at least 40% (by HPLC 280 nm).

26 Claims, 8 Drawing Sheets

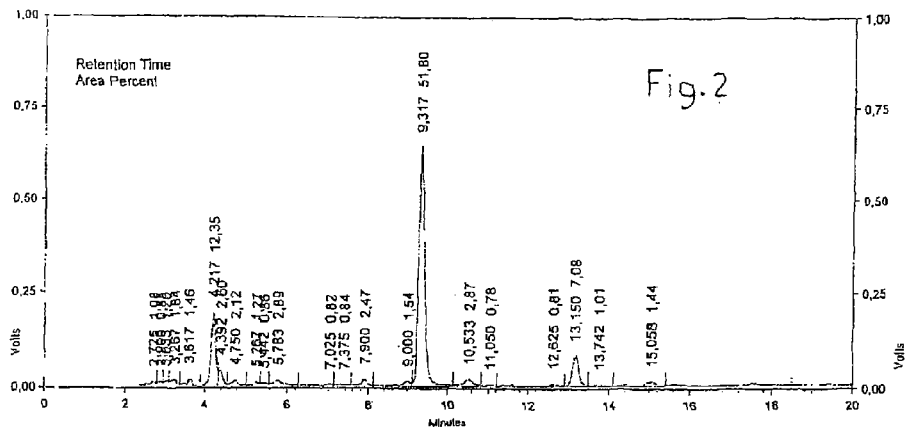
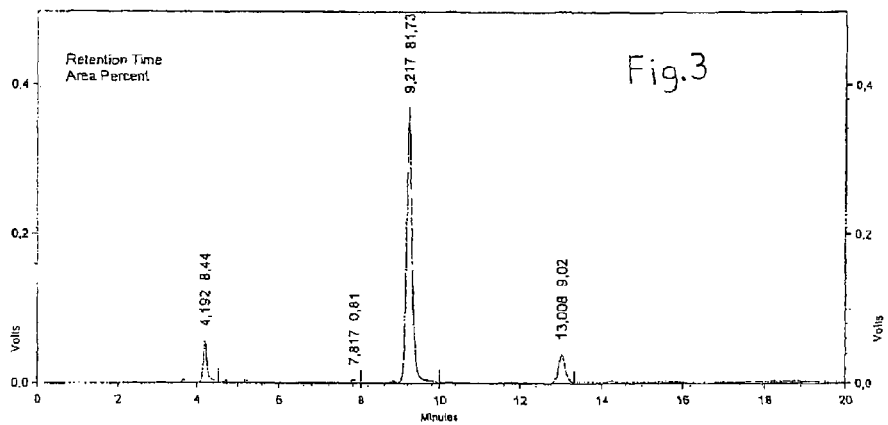
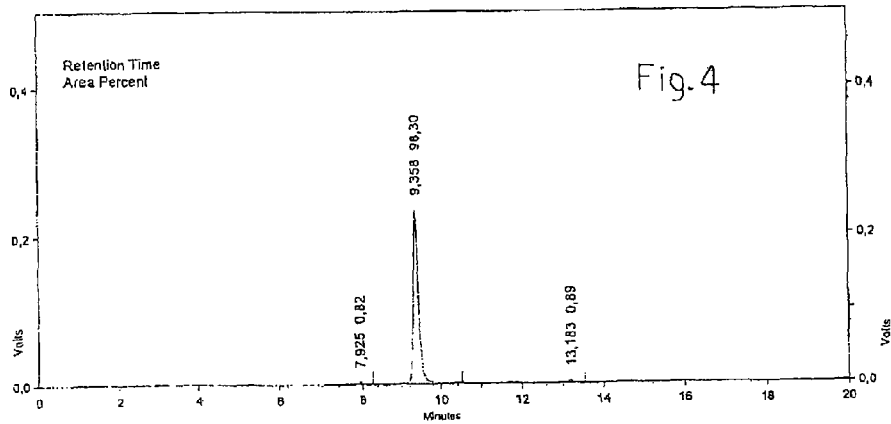

Figure 9

| Pico | t_R (min) | ESI- (m/z) | ESI+ (m/z) | ION TRAP Mass Analyzer Precursor Ion | MS/MS ESI- (m/z) | MS3 ESI- (m/z) | ESI- (m/z) | ESI+ (m/z) | m/z experimental | m/z teórica | Fórmula |
|---|---|---|---|---|---|---|---|---|---|---|---|
| 1 | 3.6 | 274.9; 166.8 | | 274.9; 166.8 | 256.6;242.8;228.8;198.8;184.8;154.8;110.9; 122.9;148.9 | 154.8; 110.9 | 275.0769 [M-H]-; 167.0360 [M-H]- | 299.0725 [M+Na]+; 191.0397 [M+Na]+ | 276.0844; 168.0422 | 276.0945; 168.0423 | C11H16O8; C8H8O4 |
| 2 | 4.3 | 152.9 [M-H]-; 122.9; 226.9; 315.0; 109.0 | 177 [M+Na]+ | 152.9; 226.9 | 122.9[M-H-30]-; 182.8;164.8;138.9; 120.9;95.1 | 120.9 | 153.0563 [M-H]-; 307.1225[2M-H]- | 177.0565 [M+Na]+ | 154.0636 | 154.063 | C8H10O3 |
| 3 | 6.6 | 349 [M-H]-; 214.9 [M-H-134]- | 373.1 [M+Na]+; 239.0 [M+Na-134]+ | 349.0 | 288.9[M-H-60]-; 258.9[M-H-90]- | 258.9; 121.8 | 349.1306 [M-H]- | 373.1262 [M+Na]+ | 350.1379 | 350.1379; 350.1392; 350.1366; 350.1419; 350.1413; 350.1318 | C19H18N4O3; C21H20N4O; C18H22O7; C24H18N2O1; C24H18N2O1; C22H19FO3 |
| 4 | 7.3 | | | | | | | | | 226.0841 | C11H14O5 |
| 5 | 16.7 | 224.9 [M-H]- | 249.0 [M+Na]+; 475.1 [2M+Na]+; 511.0 | 224.9 | 89[M-H-136]- | 89.1[M-H-136]-; 241.9; 134.8; 120.8 | 225.0760 [M-H]-; 451.1620 [2M-H]- | 249.0735 [M+Na]+ | 226.0832 | 226.0855; 226.0816; 226.0794 | C12H10N4O1; C15H11O1; C16H16O5 |
| 6 | 20.9 | 287.0 [M-H]-; 575.1 [2M-H]- | 311.1 [M+Na]+; 361.1 | 451.1; 287.0 | 256.9[M-H-30]-; 122.8 | | 287.0934 [M-H]- | 311.0892 [M+Na]+ | 288.1007 | 288.0998; 288.1023 | C18H16O5; C14H13F1N4O2 |
| 7 | 21.4 | 351.0; 337.1 [M-H]- | 361.1 [M+Na]+ | 351.0; 337.1 | 306.9[M-H-44]-;170.8[M-H-180]-;126.8; 200.8;156.9 | 170.8;126.9; 182.8;156.8;138.9;95.1;59.4 | 351.1108; 337.1304 [M-H]- | 339.1434 [M+H]+; 361.1250 [M+Na]+ | 338.1376 | 338.1379; 338.1376 | C18H18N4O3; C17H22O7 |
| 8 | 23.1 | 307.0; 363.0 [M-H]-; 319.0 | 699.2[2M+Na]+; 387.1 [M+Na]+; 307.1 | 307.0; 363.0 | 319.0[M-H-44]-;226.8;182.8;164.8;138.9 | 274.9;182.8;138.9;95.1 | 363.1084 [M-H]- | 365.1228 [M+H]+; 387.1050 [M+Na]+ | | | |
| 9 | 24.1 | 325.0 [M-H]-; 278.9; 252.9 | 349.1 [M+Na]+ | 325.0; 353.0 | 252.8[M-H-72]-; 224.8; 116.9 335.0 | 116.8 316.9;290.9;272.9;246.9;216.9;198.8;180.8;1 52.8;136.8;122.9;111.0 | 325.0967 [M-H]- | 349.1105 [M+Na]+ | 326.104 | 326.1049; 326.1055; 326.1015; 326.1067; 326.1089; 326.1002 | C13H18N4O4S1; C21H14O2O2; C16H14O4O4; C18H15F1N2O3; C8H18N2O2O2S1; C15H13O6 |
| 10 | 24.2 | 143.0; 559.2[2M-H]-; 278.9[M-H]- | 303.1 [M+Na]+; 349.0 | 559; 279 | 278.9[M-H]-; 142.8 | 142.8[M-H-136]- | 279.1296 [M-H]-; 559.2605 [2M-H]- | 303.1199 [M+Na]+ | | 352.1185; 352.1190; 352.1158; 352.1245; 352.1252 | C20H18N2O5; C17H21O1N2O4; C17H22O8; C20H20N2O2S; C28H16 |
| 11 | 24.5 | 351.0 [M-H]- | 375.1 [M+Na]+ | 351.0 | 332.9;306.9[M-H+44]-;214.9;196.8[M-H-154]-; 170.8[M-H-180]-;152.8;126.9;109.0 | 152.8;108.9 | 351.1113 [M-H]- | 375.1049 [M+Na]+ | 352.1186 | | |
| 12 | 25.1 | 319.0 [M-H]-; 639.1[2M-H]-; 182.9 | 343.1 [M+Na]+; 663.2[2M+Na]+ | 639 | 318.9;182.8[M-H-136]- | 182.8[M-H-136]-; 138.9[M-H+180]- | 319.1200 [M-H]-; 639.2380 [2M-H]- | 321.1340 [M+H]+; 343.1161 [M+Na]+ | 320.1273 | 320.1285; 320.1260; 320.1220 | C15H17F1N4O3; C17H2O6; C12H2ON2O8 |
| 13 | 25.7 | 319.0 [M-H]-; 639.1[2M-H]-; 182.9 | 343.1 [M+Na]+; 663.2[2M+Na]+ | 639 | 318.9;182.8[M-H-136]- | 182.8[M-H-136]-; 138.9[M-H+180]- | 319.1200 [M-H]-; 639.2380 [2M-H]- | 321.1340 [M+H]+; 343.1161 [M+Na]+ | 320.1299 | 320.1285; 320.1260; 320.1220 | C15H17F1N4O3; C17H2O6; C12H2ON2O8 |
| 14 | 28.6 | 473.1 [M-H]- | 497.2 [M+Na]+ | 473; 587 | 337.0[M-H-136]-;200.8[M-H-272]-; 473.1 | 200.8[M-H-272]- | 473.1849 [M-H]- | 485.1404 [M+Na]+ | 462.158 | 462.1580; 462.1591; 462.1539; 462.1625; 462.1526; 462.1652 | C29H22N2O4; C26H23F1N2O5; C30H18N6; C24H22N4O6; C23H27F1N2O5S; C23H26O10; C17H27N6O5 |
| 15 | 29.0 | 587.0; 487.1 [M-H]- | 511.0 [M+Na]+ | 487; 461 | 443.0;351.0[M-H-136]-;333.0;307.0;196.8;170.8 325.0[M-H-136]-;188.9[M-H-272]- | 335.0;198.8 332.9;306.9;214.8;196.8;170.8;152.8;126.9;1 09.0 188.8[M-H-272]- | 487.1611 [M-H]- | 511.1553 [M+Na]+ | 488.1719 | 488.1736; 488.1986; 488.1741; 488.1631; 488.1624 | C31 H24 N2 O4; C26 H24 N4 O6; C18 H32 O15; C25 H24 N6 O3 S1; C32 H24 O5 |
| | | 451.1 [M-H]- | 485.2 [M+Na]+ | | | | | | | | |

HYDROXYTROSOL CONTAINING EXTRACT OBTAINED FROM OLIVES AND SOLIDS CONTAINING RESIDUES OF OLIVE OIL EXTRACTION

CROSS-REFERENCE TO RELATED APPLICATIONS

This application is a Continuation-in-Part of U.S. patent application Ser. No. 12/524,603, filed Dec. 15, 2009. The contents of this application is incorporated herein by reference.

FIELD OF THE INVENTION

The present invention relates to a hydroxytyrosol containing extract obtained from olives and/or the solid-containing residues of olives after the extraction of olive oil. More particularly, the invention relates to the production of hydroxytyrosol-containing extracts to be used as a source of hydroxytyrosol in food, medical and cosmetic industries.

BACKGROUND OF THE INVENTION

It is now well known that olives contain a number of bioactive compounds, particularly polyphenols; among these polyphenols, hydroxytyrosol is of outstanding biological significance in view of its antioxidant, antimicrobial and radical scavenging activity.

Hydroxytyrosol is present in olives and olive oil and has the following formula:

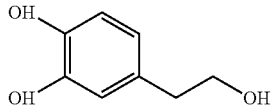 [SMILES: OCCc1ccc(O)c(O)c1]

In co-pending patent applications EP07001791 and PCT/IB2008/000173, which are incorporated by reference, process and apparatus for the production of hydroxytyrosol from olives and/or olive oil extraction residues are described, which aim at the production of hydroxytyrosol-containing products or extracts to be used as a source of hydroxytyrosol in food, medical and cosmetic industries. The content of the above applications is hereto incorporated by reference.

Production of hydroxytyrosol from olives residues after oil extraction was and is actively investigated; an efficient extraction process could be very profitable especially because the major amount of hydroxytyrosol and hydroxytyrosol precursors initially present in the olives remains in the residues from olive oil production and only a minor part is found in the oil. Extra virgin olive oil normally contains 1-20 ppm of hydroxytyrosol.

The residues of olive oil extraction of interest for the present application exclude the olive tree leaves, because the leaves are removed before oil extraction. Moreover, hydroxytyrosol extraction from leaves faces different starting compositions (and therefore different extraction problems) than extraction from olives or olive residues.

The residues of olives as obtained from olive oil extraction processes of interest for the present application can be classified as:

pomaces, i.e. the solids containing residues of the pressing (in Spanish: orujo), of the three-phases process (orujo), or of the two-phases process, in which no water is added to the chopped olives in the centrifugation step (in Spanish: alperujo). Orujo, alperujo and defatted orujo contain a high amount of water (45% to 70%). Extraction residues also comprise orujillo, the olive dry solids, after orujo oil extraction that contains less than 15% water and is nearly free from oil residues.

The green olives extracts of the invention are preferred to the extracts of residues of olive oil production in view of their greater amount of hydroxytyrosol and of the reduced content of hydroxymethylfurfural.

For the purposes of the present description the term "pomaces" or "solid residue" is designating both "orujo", "defatted orujo" "orujillo" and "alperujo". Preferred starting materials for the present invention are olives, more preferably green olives, and pomaces.

It is well known that several sensory properties are elicited by olive polyphenols in extra virgin and virgin olive oils. The sensory aspect of these olive oils has great repercussions on its acceptability by consumers. Some phenols mainly elicit the tasting perception of bitterness; however, other phenolic molecules can stimulate the free endings of the trigeminal nerve located in the palate and also in the gustative buds giving rise to the chemesthetic perceptions of pungency, astringency and metallic attributes.

Oleuropein, the phenolic compound that makes the fruit of the olive bitter, is water-soluble rather than fat-soluble, and it gets poorly transferred into the oil when the fruit is pressed, thus average content of oleuropein in extra virgin and virgin olive oils is from 1 ppb to 11 ppm.

Oleuropein is present in olives and olive oil and has the following formula:

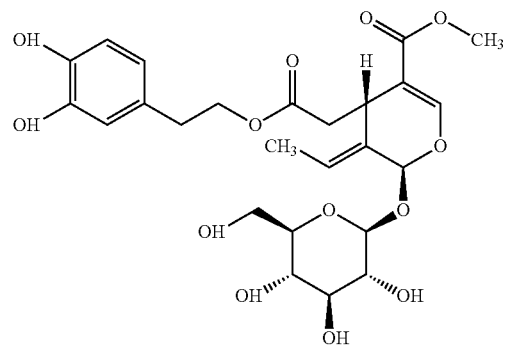 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1]

Nevertheless, a number of oleuropein related compounds are more oil soluble than oleuropein itself, and do end up at a higher content in the oil, in the form of isomer (or isomers) of oleuropein aglycone (e.g.: aldehydicic form of oleuropein aglycone, AOA), and dialdehydic form of elenolic acid linked to hydroxytyrosol or tyrosol, respectively named 3,4-DH-PEA-EDA and p-HPEA-EDA, that are the olive polyphenols mainly responsible for the bitter taste according to Gutierrez-Rosales and co-authors, J. Agric. Food Chem. 2003, 51, 6021-6025.

Oleuropein aglycone (e.g.: aldehydic form of oleuropein aglycone) is present in olive oil and in crushed olives during oil extraction process and has the following formula:

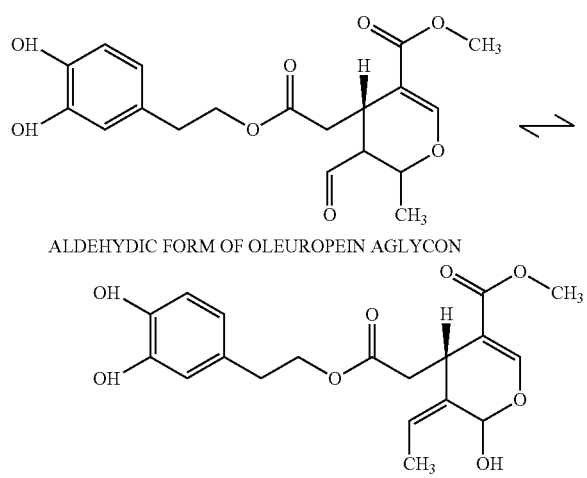

ALDEHYDIC FORM OF OLEUROPEIN AGLYCON

It is known to carry out acid hydrolysis of the pomaces (or of vegetation water) to have the cleavage of the ester bond in the oleuropein molecule and obtain hydroxytyrosol.

U.S. Pat. No. 6,361,803, which is incorporated by reference, discloses extraction of hydroxytyrosol (and other compounds) by neutral or acid hydrolysis of olive pulp residues at reflux for one hour (ex.12). The extracted water solution is loaded on an absorption XAD-7 column that is eluted with methanol to recover the extracted hydroxytyrosol. U.S. Pat. No. 6,361,803 requires the use of organic polar solvents, to recover hydroxytyrosol with a minimum purity grade, in addition (ex.12) freeze precipitation of some impurities from the methanol solution is necessary. Polar aqueous solvents are selected among methanol, ethanol, acetonitrile or acetone, while polar organic solvents are selected, for example, among esters, amides, dimethyl sulfoxide, dioxane, DMF and their mixtures. Most of these solvents are toxic and very difficult to completely eliminate from the desired hydroxytyrosol product. Accordingly, traces of the utilized solvents will be found in the final product even after several purification steps, thus rendering the hydroxytyrosol obtained according to this process not suitable for a safe application in the alimentary, cosmetic and pharmaceutical field. Moreover, the final product is not suitable for use in fortifying foods, particularly edible oils, without use of ethanol and acetic acid as additives to the extract to obtain a stable food product: the resulting food product (oil plus hydroxytyrosol containing extract, ethanol and acetic acid) is not acceptable in the food industry.

WO 2004/005228, which is incorporated by reference, discloses hydrolysis at room temperature of vegetation water obtained from olive oil extraction by incubation of the acidified vegetation water for at least two months and preferably 6-12 months until at least 50% (preferably 90%) of the oleuropein originally present in the vegetation water has been converted to hydroxytyrosol. The incubated vegetation water is extracted with an organic solvent, for example ethyl acetate, or it is contacted with a supercritical fluid ($CO_2$), to produce a fraction rich in hydroxytyrosol. The main problems of this process are the very long time required for the incubation of the acidified vegetation water and the use of organic solvents, that should be avoided, particularly when the final product obtained is to be used in the alimentary, cosmetic and pharmaceutical field.

U.S. Patent Application Publication 2004/0102657, which is incorporated by reference, discloses acidic hydrolysis with a steam explosion process at high temperatures (about 190-220° C.). The obtained solution is firstly partially purified on a column with non activated ion exchange resin and subsequently loaded on a XAD non-ionic column, from where the hydroxytyrosol is eluted with methanol or ethanol. The process results in a poor yield in hydroxytyrosol, considering the process in its entirety.

EP 1623960, which is incorporated by reference, 0, discloses a process of recovery of hydroxytyrosol, and tyrosol, from alpechin by means of filtration in a complicated plant consisting of three units (Ex. 1) and subsequent separation. The tyrosol is then oxidated to hydroxytyrosol in a protic solvent (alcohol or water) to obtain a final product that is semi-synthetic. Additionally, EP 1623960 discloses that concentration by nanofiltration and reverse osmosis of vegetation waters (alpechin) are carried out at neutral or alkaline pH (claim 4). This process has two important problems. A first drawback is that hydroxytyrosol degradation increases at neutral and alkaline conditions giving unwanted products that are difficult to remove, and, in addition, due to the fact that no acid hydrolysis is carried out the oleuropein content should be still high. Secondly, the obtainable concentration factor is poor, thus the maximum concentration allowed for hydroxytyrosol according Ex-1 (see table 1) is in the range from 1.2 to 1.6 g/L.

U.S. Patent Application Publication 2004/0176647, which is incorporated by reference, discloses an extraction process of phenols from alperujo under stirring at 180-240° C. in autoclave, in water. No acid is added, but the thermal treatment results in a "liberation of acetyl groups" and in an alleged consequent reduction of the pH (page 3, first paragraph). Nevertheless, at the pHs produced in the described conditions hydrolysis of oleuropein is far to be complete, meaning two things, lower hydroxytyrosol yields and remaining hydrolysed oleuropein, that as we discuss above is causing non-pleasant taste in food products containing such extracts, that are thus not suitable for food applications. The products are tyrosol and hydroxytyrosol, that are separated by HPLC with sulphuric acid/acetonitrile eluent.

Summarizing, the above mentioned techniques are either too long or too complex, or too harsh, or all of the above; this results in that the amount of remaining oleuropein, i.e. the amount that is not hydrolyzed, and/or the amount of the hydrolysis by-products such as hydroxymethylfurfural is high enough to make difficult the subsequent purification steps.

Obtaining a good source of hydroxytyrosol is very important for the fortification of foods, especially of edible oils. Extracts should not transfer to oils any bitter polyphenolic substances, however, the health beneficial compounds, namely hydroxytyrosol, are always associated to bitter polyphenols in the known extracts.

Frank and co-authors in *J. Agric. Food Chem.* 2001, 49, 231-238 disclose a procedure called "taste dilution analysis" in order to point out the sensory threshold of bitter for oleuropein derivatives. Bitterness was assessed by preparing serial dilutions of samples in water and then tasting them according to increasing concentration, until the concentration at which the diluted sample can be differentiated from water as judged in a triangle test is found.

It was also shown that at least for these compounds there is no direct correlation of bitterness with the absorbance at 225 (the K225 value): Mateo et al. *J. Am. Oil Chem. Soc.* 2004, 81, 71-75, verified the correlation between the aldehydic form of oleuropein aglycone (obtained by hydrolysis of oleuropein with β-glucosidase from almonds purchased from Sigma) and bitterness.

Andrewes et al., J. Agric. Food Chem. 2003, 51, 1415-1420, assessed the relationship between polyphenols and olive oil pungency; p-HPEA-EDA was the key source of the burning sensation found in many olive oils.

In 2005, Beauchamp and co-authors, Nature 2005, 437, 45-46, measured the pungent intensity of p-HPEA-EDA isolated from different extra virgin and virgin olive oils confirming this molecule is the principal agent in extra virgin and virgin olive oils responsible for throat irritation.

Additionally, the bitter and pungent polyphenols present in olive oil, are also presents in olives and are also responsible for their bitterness and pungency, those being the ones that best correlate with the bitterness attribute the oleuropein and the aldehydic form of oleuropein aglycone. The crushing of olives to prepare olive oil or olive extracts produces the hydrolysis of oleuropein by endogenous β-glucosidase rendering oleuropein aglycone as transient specie that forms the aldehydic form of oleuropein aglycone. Thus, the use of olive extracts containing oleuropein and/or the aldehydic form of oleuropein aglycone can modify the taste of foods in which the aforementioned extract is incorporated, resulting in a lower acceptance by consumers.

Summarizing, any way set up in order to increase antioxidant capacity using techniques based on fortification of foods with olive polyphenols, should not alter food natural organoleptic characteristics, nor increase the amount of the bitter tasting olive polyphenols, otherwise incurring with the subsequent alteration of organoleptic properties of the food, thus causing non-pleasant taste due to excessive bitterness, pungency and/or astringency, and subsequently causing rejection of the fortified food from many consumers.

It is known to add polyphenols and hydroxytyrosol to food products.

U.S. Pat. No. 6,942,890 which is incorporated by reference, discloses a method of fortifying food products adding to such products solid matter derived from olive fruits, resulting in an increase of the level of antioxidants, particularly of olive polyphenols.

It has also to be noted that all the previously mentioned techniques allow to obtain a fortified food with an increased content of total olive polyphenols but with a low content in hydroxytyrosol with respect to the total olive polyphenols content, due to the fact that most of the polyphenols incorporated to the fortified food are secoiridoids, oleuropein related compounds as oleuropein aglycone (AOA), 3,4-DHPEA-EDA and p-HPEA-EDA, at a higher content than hydroxytyrosol, and that those olive polyphenols are mainly responsible for the bitter taste and pungency of the fortified oil. The incorporation of these secoiridoids, able to produce undesirable changes in the organoleptic properties of the fortified food, is in fact directly related with the source of olive polyphenols used in all the previously mentioned techniques, which in fact present a low content in hydroxytyrosol and/or a low purity degree.

A few studies addressed the bioavailability of polyphenolic compounds in olive showing that the absorption of olive oil phenolics is probably larger than 55-66 mol %, and that the absorption of hydroxytyrosol is dose-dependent, suggesting that olive oil phenolics are absorbed from the intestine, that tyrosol and hydroxytyrosol are incorporated in lipoprotein fractions, and that hydroxytyrosol is excreted in urine as glucuronide conjugate. The incorporation of phenolic compounds from olive oil in LDL particles has been proposed as the mechanism by which olive phenolics may protect LDL particles from peroxidation.

The EFSA Panel on Dietetic Products, Nutrition and Allergies (NDA) concludes that a cause and effect relationship has been established between the consumption of olive oil polyphenols (standardized by their content of hydroxytyrosol and its derivatives) and protection of blood lipids from oxidative stress.

According to Regulation (EC) No 1924/2006 of the European Parliament and of the Council of 20 Dec. 2006 on nutrition and health claims made on foods, a claim that a food is sugars-free, and any claim likely to have the same meaning for the consumer, may only be made where the product contains no more than 0.5 g of sugars per 100 g or 100 ml.

SUMMARY OF THE INVENTION

It is an aim of the present invention to solve the above mentioned problems and to provide olive extracts to be used as a source of hydroxytyrosol to prepare fortified food oils and products in general and dietary supplements for protection of blood lipids from oxidative stress, thus preventing or treating cardiovascular diseases, plaque build-up in the arteries, arterial hypertension, and metabolic syndrome, but avoiding non-pleasant alterations of organoleptic properties of the fortified foods.

In fact, the applicant found that generation of by-products is a much bigger problem in the production of hydroxytyrosol extracts than it was previously thought, as it appears from the above discussed prior art documents: the starting materials, especially olives and pomaces, contain inter alia a high amount of phenolic compounds in the form of glucoside and/or its esters including oleuropein, ligustroside, verbascoside and several flavonoids. Several other natural compounds are present. It is very easy to degrade the starting compounds into a plethora of by-products.

As by-products must be eliminated to purify hydroxytyrosol, in the known art the use of organic solvents is required in order to purify the hydroxytyrosol during the subsequent purification steps on chromatographic columns. The use of organic solvents, for example methanol, when eluting from a resin column, is inconvenient, particularly when the final product obtained is to be used in the alimentary, cosmetic and pharmaceutical field.

Moreover, the known hydroxytyrosol-rich extracts are not suitable to be used as additives for foods, especially edible oils.

Therefore, there is the need for a hydroxytyrosol containing extract that is rich in hydroxytyrosol and has low content of starting products and of bitter products such as oleuropein and verbascosides, and of by-products, particularly hydroxymethylfurfural and in general has a very low content in sugars and in salts.

It is an aim of the present invention to solve the above mentioned problems and to provide a hydroxytyrosol extract from olives and/or olive oil extraction by-products that is simple to obtain, not expensive and that is a high purity product free from organic solvents and suitable for use as additive for food, cosmetics etcetera.

Such aim is achieved by means of the present invention that provides an extract, as obtainable by extraction from a starting material selected from olives and/or pomaces, residues of olives after the extraction of olive oil, characterized in that said extract contains hydroxytyrosol and tyrosol, the amount of sugars per 100 g or 100 mL of extract is 0.5 g or less, the residual content of Benzo[a]pyrene in said extract is less than 2 microg/Kg (weight BaP/weight of extract as dry matter), containing a weight ratio of hydroxytyrosol to hydroxymethylfurfural of between 45:1 and 10000:1 and in that the content of hydroxytyrosol in said extract is at least 0.5% (w/w) and the hydroxytyrosol purity is at least 40% (by HPLC 280 nm).

More particularly, a preferred olive extract is that one obtained according to the process hereinafter disclosed, having a content in hydroxytyrosol of at least 0.5% by weight (w/w), and a purity of hydroxytyrosol of at least 40% (by HPLC at 280 nm). This extract is free of organic solvents (the residual content of organic solvents is less that 1 ppb and preferably 0 ppm) and substantially free of sugars, and the content in hydroxytyrosol of that extract is at least 0.5% (w/w) and the purity of hydroxytyrosol is at least 40% (by HPLC at 280 nm). A hydroxytyrosol content of at least 10% (w/w) is preferred, and more preferably at least 35% (w/w); the purity of hydroxytyrosol at 80% is preferred, and more preferably at 90% (by HPLC at 280 nm).

The substantial absence of even minimal traces of organic solvents such as methanol, ethanol, isopropanol that are employed in the purification steps of the prior art, is of great importance for the intended use of the aforementioned extracts.

Additionally, some of the polyphenols present in olives are responsible for their bitterness, the ones that best correlate with this attribute being the oleuropein and the aldehydic form of oleuropein aglycone. Thus, the use of olive extracts containing oleuropein and/or the aldehydic form of oleuropein aglycone can modify the taste of foods in which the aforementioned extract is incorporated, resulting in a lower acceptance by consumers.

Olive extract rich in hydroxytyrosol obtained according to the invention process (as per co-pending U.S. application Ser. No. 12/524,603) is virtually free of oleuropein and of the aldehydic form of oleuropein aglycone, the total amount of each compound being less than 500 ppm (their detection limit), because no organic solvent is used, where these molecules, much more hydrophobic than hydroxytyrosol, are more soluble, for obtaining the extract, together with the combination of purifying steps used, chromatographic columns, for obtaining the extract.

Also the olive extract rich in hydroxytyrosol obtained according to the invention process has a very low content of hydroxymethylfurfural, being the ratio hydroxytyrosol/hydroxymethylfurfural (w/w) higher than 45:1 before column purification or higher than 9000:1 after purification steps, because the controlled extraction conditions pH time and temperature, together with the combination of purifying steps used, chromatographic columns, for obtaining the extract.

An additional advantage of the above mentioned olive extracts is the purification from the residues of pesticides present in raw materials, i.e. in the olives and olive pomaces. Thus, potentially toxic chemicals such as insecticides, herbicides, fungicides, rodenticides, etc. . . . , such as: diuron, terbuthylazine, simazine, α-endosulfan, and β-endosulfan may be present in the starting material.

Hydroxymethylfurfural (HMF), also 5-(Hydroxymethyl) furfural, is an organic compound derived from dehydration of certain sugar, especially in acidic conditions. This yellow low-melting solid is highly water-soluble. The molecule consists of a furan ring, containing both aldehyde and alcohol and functional groups. HMF has been identified in a wide variety of heat-processed foods including milk, fruit juices, spirits, honey, etc. . . .

HMF is a natural component in heated food but is usually present in low concentrations. The daily intake of HMF may underlie high variations due to individual consumption-patterns. It has been estimated that in a western diet, about 5-10 mg of HMF are ingested per day from food.

In former times, HMF was used in food for flavoring purposes, but in Europe this practice now is suspended. HMF is also found in cigarette smoke.

In vitro tests and studies on rats suggest potential toxicity and carcinogenicity of HMF. In humans, no correlation between intakes of HMF and disease has yet been demonstrated.

Polycyclic aromatic hydrocarbons (PAHs), are potent atmospheric pollutants that consist of fused aromatic rings and do not contain heteroatoms or carry substituents. PAHs occur in oil, coal and tar deposits, and are produced as byproducts of fuel burning (whether fossil fuel or biomass). As a pollutant, they are of concern because some compounds have been identified as carcinogenic, mutagenic and teratogenic. PAHs are also found in cooked foods. Studies have shown that high levels of PAHs are found, for example, in meat cooked at high temperatures such as grilling or barbecuing, and in smoked fish. As olive oil extraction residues are complex materials it is possible that harsh conditions in temperature (i.e. steam explosion extraction) during olive polyphenol extraction could produce such PAHs at residual levels, being then desirable that a process to extract olive polyphenols avoid such PAHs residual levels formation.

Benzo[a]pyrene (BaP) is commonly used as an indicator species for PAHs contamination and most of the available data refer to this compound.

AIIs, HMF, PAHs and above mentioned pesticides have molecular structures (e.g. the core of triazines in most of the pesticides) capable of interacting with the absorption resins and then are eluted from the resin together with other components of the extract when using organic solvents. Thus the methods of preparing extracts from olives based on the use of an absorbent resin and subsequent elution with organic solvents must exercise extreme quality control on the raw material pesticide residues, but also in the hydrolysis and extraction process of olive polyphenols in acidic conditions from olive materials containing sugar able to degrade to HMF, since the absorption resin can act as a trap for PAHs, HMF and these pesticides, that will concentrate on the resin and then elute when an organic solvent is used to recover the hydroxytyrosol present in the olive.

The above problem was solved by the invention with the preparation of an olive extract rich in hydroxytyrosol, due to the fact that the non-ionic absorption resins were specifically selected to elute the active compounds of the said extract by use of water only, or of an aqueous solution basified and not by the use of organic solvents.

The process of preparing the extract of the invention entails the acidic hydrolysis in water of the starting materials at a temperature not exceeding 140° C., preferably within the range from 70° C. to 130° C. and most preferably above the reflux temperature, in the range of 110° C. to 130° C. and in a pressurized condition, e.g. in an continuous sterilization system, at a pressure within the range of atmospheric pressure to 10-20 psi above the atmospheric pressure. The pH of the acidified mixture that undergoes the hydrolysis is within the range of 1.0 to 6.0. The mixture after the hydrolysis is clarified by physical methods known in the art, e.g. by filtering and/or centrifuging, to remove the suspended solids from the hydrolysis water solution, and to obtain a clarified solution substantially free of solids in suspension.

The starting materials are olives or pomaces, i.e. the above defined residues from olive oil extraction. Preferred olives are green olives, pomaces are preferably free from oil. Oil is removed either before or after the hydrolysis step by means known in the art (e.g. those used to prepare defatted orujo or orujillo) or by use of diatomaceous earth or other filter means.

According to the invention the above steps (acid hydrolysis and clarification) are followed by the steps of loading the product thus obtained in at least one chromatographic column of an acid activated anion exchange resin, and of eluting the products retained in said chromatographic column with water.

In a preferred aspect, the invention provides for a further purification step carried out by loading the water-eluted solution from the first column (anion exchange) in at least one chromatographic column of adsorbent non-ionic resins and of eluting the products retained in said second chromatographic column with water.

According to a further aspect of the invention the liquid product is concentrated e.g. by reverse osmosis concentration. According to a further step, after chromatographic purification and reverse osmosis concentration, the resulting liquid product is brought to a solid form, e.g. by freeze-drying, vacuum rotaevaporation or spray drying, with or without carriers such as maltodextrines.

The extract of the invention has a ratio by weight of hydroxytyrosol:oleuropein that is greater than 200:1, preferably also a ratio (by weight, i.e. w/w) of hydroxytyrosol: aldehydic form of oleuropein aglycone that is between 5:1 and 850:1.

Additionally, in a preferred embodiment the extract according to the invention is free from oleuropein and aldehydic form of oleuropein aglycone (by HPLC 280 nm).

According to another aspect, the invention extract has a ratio hydroxytyrosol:tyrosol that is greater than 55:1 by weight, preferably within the range of 55:1 to 618:1.

Moreover, the extract is free from organic polar solvents.

A further object of the invention is the use of an extract as above disclosed as a source of hydroxytyrosol in the food industry as additive or as functional ingredient; as a source of hydroxytyrosol in the cosmetic industry or as a source of hydroxytyrosol in the pharmaceutical industry. To put it in other words, it is an object of the invention a process of preparing an enriched food, cosmetic or pharmaceutical product, wherein an extract according to the invention is added to said product.

The invention provides several advantages over the prior art techniques.

First of all, the hydrolysis step is carried out, according to the present invention, using just water and mineral acid, keeping the temperature in the claimed range preferably above the reflux temperature, using a combination of heating and pressure. When pressure is applied together with the claimed heating temperature, the resulting hydrolysis reaction is almost completed in about half an hour, without significant formation of by-products and with a very good conversion of the starting material (oleuropein) into the final desired product (hydroxytyrosol). The hydrolysis step according to the present invention allows to obtain, in a short time, a very good yield in hydroxytyrosol together with a quite complete absence of those by-products, that are difficult to eliminate and which are instead formed, according to the prior art, in significant amounts.

The hydrolysis step, carried out according to the invention, provides for another advantage. The combined use of acids and temperature, beside its main objective, that is to carry out the hydrolysis with a good conversion rate and avoiding the formation of detrimental by-products, results in a sterilization of the mixture. In fact, the hydrolysis step provides a sterilization of the water solution, i.e. of the products involved, that is very useful, as the starting material (for example pomaces) used in the processes for the preparation of hydroxytyrosol, usually comes from already treated materials, and generally requires some depuration-sterilization pre-treatments, to give a safe hydroxytyrosol final product. Said depuration-sterilization pre-treatments are often complex treatments and require additional process steps that, at the end of the full process, result in a lower yield in the desired final product. According to the present invention, the hydrolysis step contemporaneously allows to carry out the hydrolysis reaction and provides for the necessary sterilization of the products involved, thus avoiding the necessity to carry out any sterilization step on the starting material as well as providing for a hydrolysed material that is ready for further uses, without any additional sterilization treatment.

In addition, the hydrolysis step is followed by at least a purification step, which is carried out by loading the product obtained from the hydrolysis step in at least a single chromatography column system or in a two chromatography columns system and eluting the hydroxytyrosol retained in said chromatographic columns with water. In this case, as there are very low amounts of by-products coming from the hydrolysis step, it is possible to make use of a chromatographic column that can be eluted with water in the absence of any organic solvent, either alone or mixed with water. This means that no organic solvents are contacted with the hydroxytyrosol, thus obtaining a purified hydroxytyrosol that is particularly suitable to be used in the alimentary, cosmetic and pharmaceutical field.

Another advantage of the present invention is due to the concentration step, that allows to enrich the hydroxytyrosol content after the purification steps. These purification steps produce a liquid extract, substantially free from sugars and salts, resulting in a very important reduction of the osmotic pressure during the concentration step of the purified liquid extract permitting thus a very high concentration factor (until 350 times). This concentration step provides a "concentrate" characterized by a high content of hydroxytyrosol, which can be directly used for further treatments. According to the prior art, where no "concentration" steps are usually provided or when provided they have poor concentration factors (about 2 to 5 times) due to the lack of a previous purification that removes sugars and salts, in the described processes for hydroxytyrosol preparation, the hydroxytyrosol concentration in the processed solutions/dispersions is always very low, thus resulting in the necessity to operate with great volumes with consequent lower yields in the final product.

Always according to the present invention, the possibility to obtain a solid final product that is not mixed with any carrier, for example maltodextrines, gives the opportunity to formulate purified hydroxytyrosol according to its final intended use and according to any formal requirement, possibly required.

As above mentioned, an additional advantage of the invention's olive extracts is the purification from the residues of pesticides present in raw materials, i.e. in the olives and pomaces.

BRIEF DESCRIPTION OF THE DRAWINGS

The invention will now be further disclosed in greater detail with reference to the enclosed non-limiting drawings wherein:

FIGS. 2-4 are chromatograms of three hydroxytyrosol containing products according to three embodiments of the invention process.

Collection of eluate fraction is completed after 9.8 BV avoiding ratios of hydroxyrtyrosol/Tyrosol lower than 55.

Figure 7:
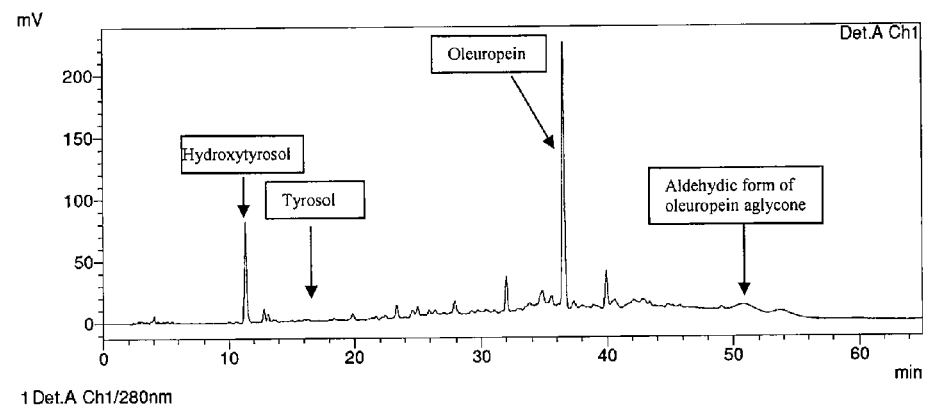

FIG. 7 is a chromatogram of hydrolysis reaction of oleuropein.

Figure 8A:
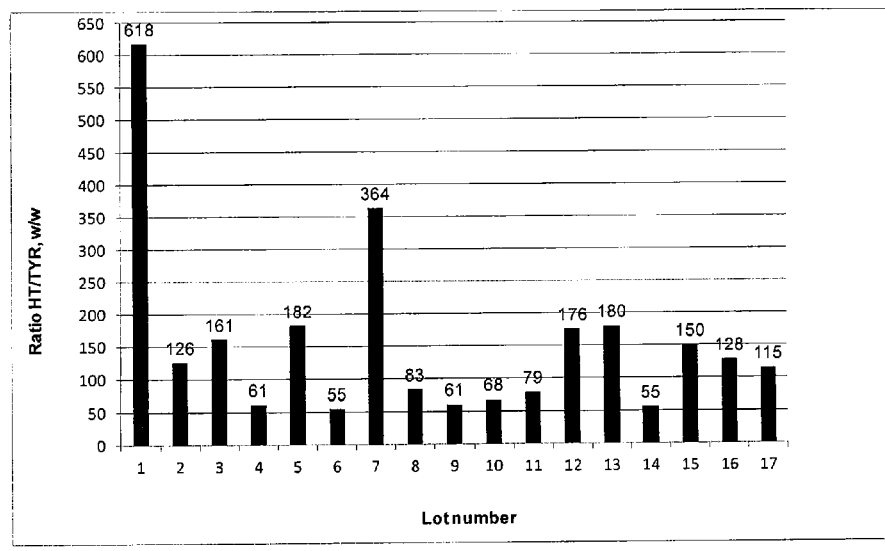

FIG. 8a is a graphical representation of ratio hydroxytyrosol/tyrosol (w/w) in 17 different production lots of olive extracts production from orujillo.

Figure 8B:
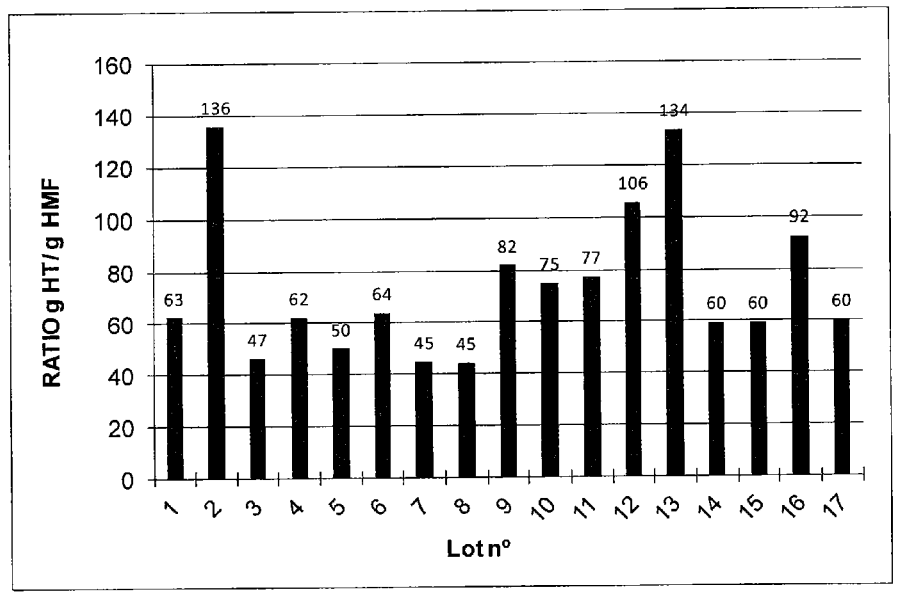

FIG. 8b is a graphical representation of the ratio hydroxytyrosol/hydroxymethylfurfural (w/w), at the crude aqueous extract after centrifugation in 17 different production lots of olive extracts production from orujillo.

FIG. 9 shows the ion species detected in purified olive extract in liquid form having a hydroxytyrosol concentration of 41.5% (w/w) with an HPLC purity of 94.8% and a ratio hydroxytyrosol/tyrosol (w/w) of 110/1 obtained according to Example 15 on the HPLC-DAD-MS systems.

Figure 10:
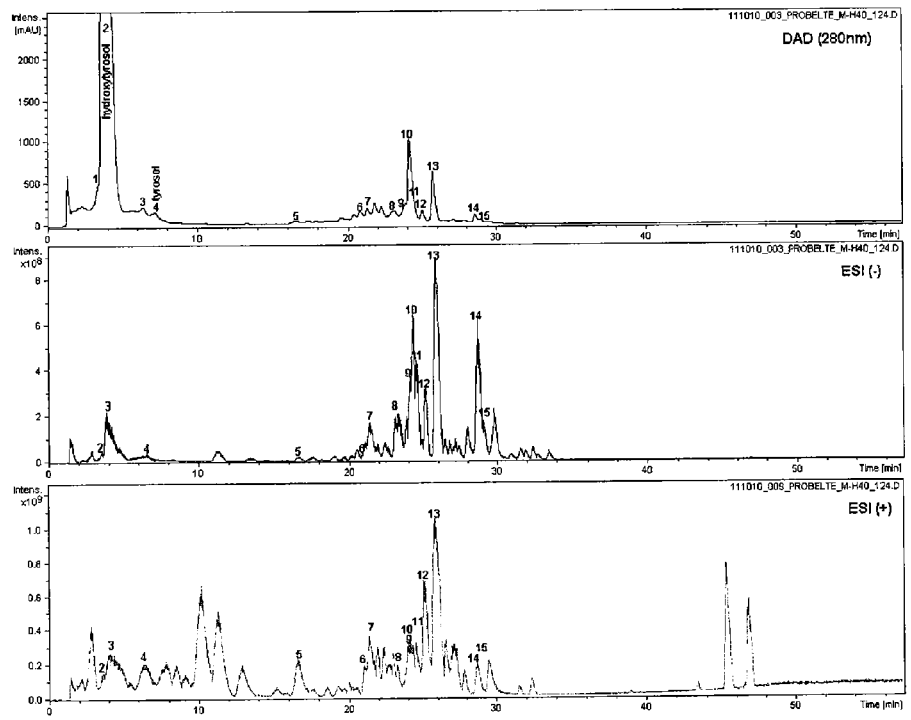

FIG. 10 is a Chromatogram DAD (280 nm); BPC (Base Peak Chromatogram) in negative (−) and positive (+) ionization mode, for purified olive extract in liquid form having a hydroxytyrosol concentration of 41.5% (w/w) with an HPLC purity of 94.8% and a ratio hydroxytyrosol/tyrosol (w/w) of 110/1 obtained according to Example 15 dissolved in MeOH 0.1% HCOOH 100 mg/ml.

Figure 11:
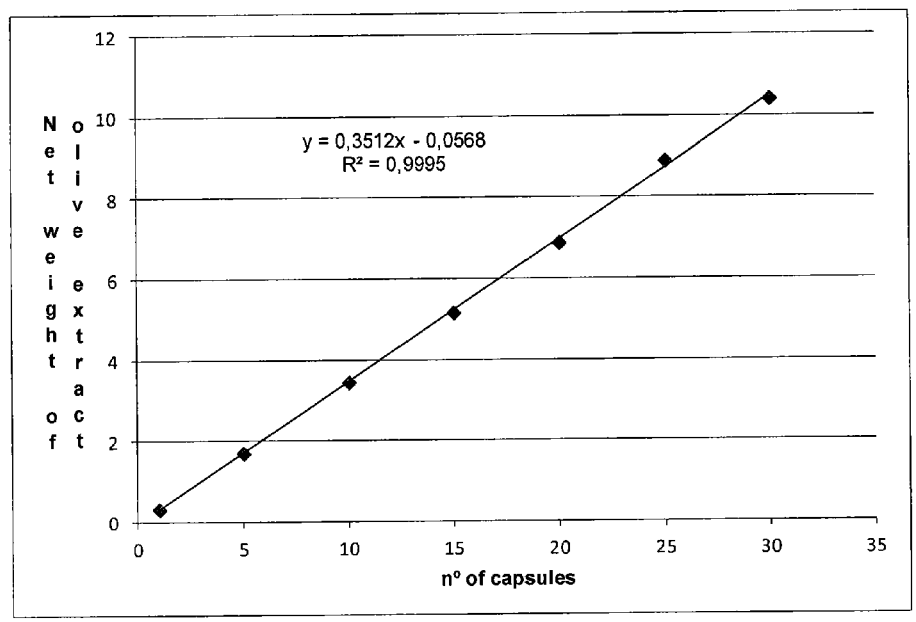

FIG. 11 is a graphical representation of a number of capsules vs. net weight of olive extract inside the dietary supplement.

Figure 12:
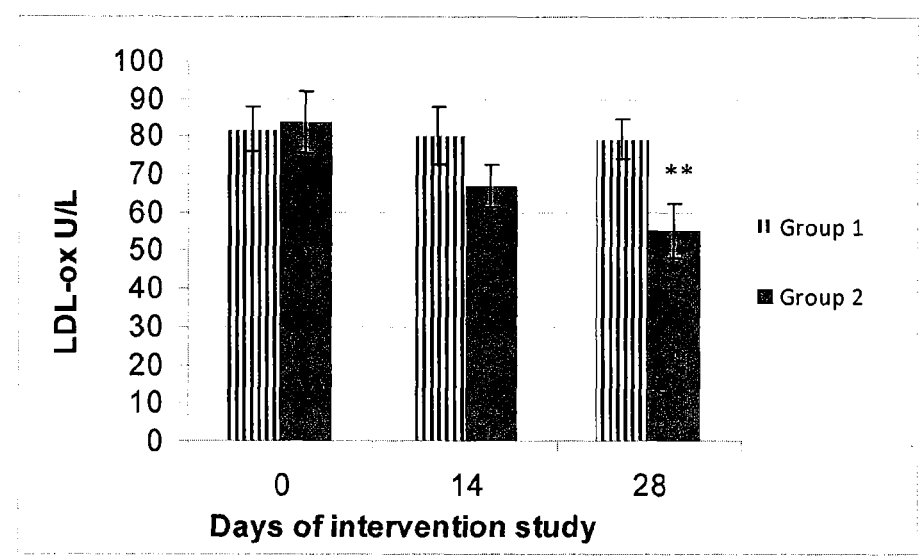

FIG. 12 is a graphical representation of the plasmatic level of oxidized LDL in the participants of the groups 1 and 2 of the intervention study. The difference at the level of oxidized LDL was determined as statistically significantive when compared Group 2 with the control Group 1, p<0.01 (Tukey's Test).

DETAILED DESCRIPTION OF THE INVENTION

Figure 1:
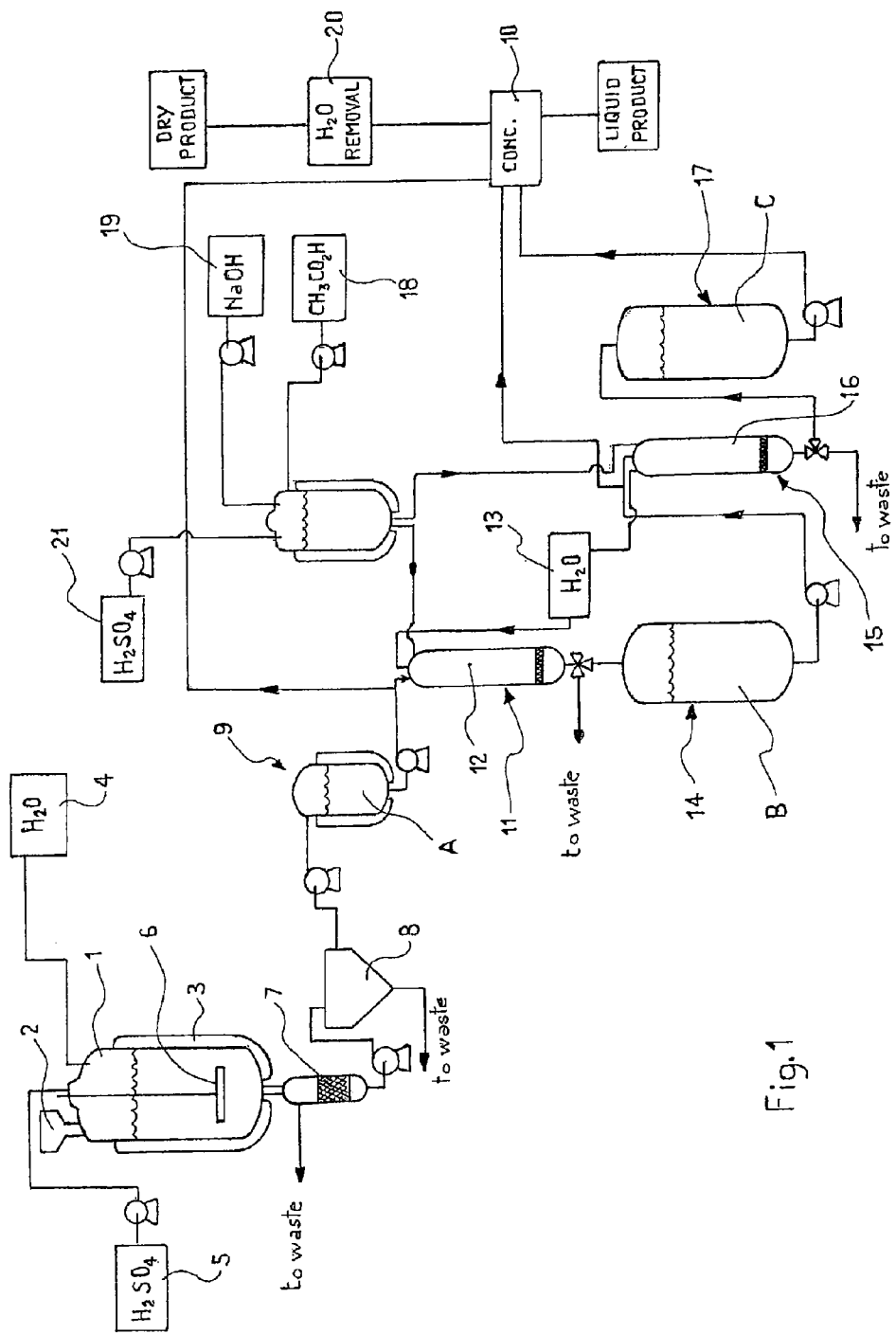
FIG. 1 is a schematic view of an apparatus according to an exemplary embodiment of the invention.

With reference to FIG. 1, the invention apparatus comprises a means, or reactor, 1, preferably a continuous sterilization system, in which the hydrolysis according to the invention process is carried out.

As previously mentioned, the hydrolysis is carried out at a temperature that does not exceed 140° C., in a reactor. Preferably the temperature range is 70 to 130° C. and most preferably it is above reflux temperature, in a range 110 to 130° C., at a pressure of 10 to 20 psi above the atmospheric pressure. and for a time length within the range of 15 to 45 minutes. Preferably, the hydrolysis temperature is within the range of 118 to 126° C. and in the most preferred embodiment the hydrolysis is carried out at 120-121° C., at 15 psi (over the atmospheric pressure) for 30 minutes. A preferred reactor is a continuous sterilization system.

The continuous sterilization system 1 is provided with feeding means 2 for feeding to it the starting materials, namely the residues, or by-products, of olive oil extraction, namely pomaces (i.e. the solid residues of the pressed olives).

Continuous sterilization system 1 is suitable to treat the starting materials in a continuous process rather than batchwise. Heating means 3 for heating the reactor 1 to the above mentioned temperatures are provided in a known way, e.g. as a jacket around the reactor. Reactor 1 is also provided with a supply of demineralized water 4 and with means 6 to stir the water mixture of starting product. Usually, the ratio water to solids is within the range of 1:1 to 4:1.

The hydrolysis process is carried out at a pH of 1.0 to 6.0, preferably of 1.0 to 3.0. The required amount of acid, preferably sulphuric acid, is obtained from acid tank 5.

The combination of acidic conditions and of temperature in the claimed ranges results in a hydrolysis process that is fast and efficient and can last for 30 minutes only, at 120-123° C. and a pressure of 15 psi above the atmospheric pressure. Moreover, the process also results in the sterilization of the hydrolysis products.

The outlet of continuous sterilization system, i.e. reactor, 1 is connected with a filter 7 for removing solids from the reaction mixture containing hydroxytyrosol and other phenols. The filtered portion is then sent to a further separation means, preferably a centrifuge 8, where further solids are removed from the reaction mixture to obtain a liquid substantially free from suspended solids, i.e. a solution that is suitable for the following purification. The clarified liquid after centrifugation has a brownish color and is preferably stored in reservoir 9. The clarified liquid A is now containing hydroxytyrosol, a residue of oleuropein and minor amounts of phenols and other products. FIG. 2 chromatogram shows the composition and the percent of the detected compounds in this liquid and is obtained by HPLC at 280 nm; the major peak at 9.317 minutes is hydroxytyrosol and the peak at 13.150 minutes is tyrosol.

According to a preferred embodiment of the invention, liquid A is concentrated by evaporation or tangential flow filtration (TFF), (e.g. by using a reverse osmosis system). The concentration step can be carried out on liquid A directly or, preferably, after a purification step by means of at least one chromatographic column. To this end, storage tank, or reservoir, 9 is connected with means of concentrating 10, e.g. by TFF or preferably by reverse osmosis, and to purification means.

Purification means comprises in one embodiment a single column system comprising a chromatographic column of a resin selected from acid activated anion exchange resins. In another preferred embodiment purification means comprises, in addition to the above mentioned first column of acid activated anion exchange resins at least a further, second, chromatographic column of a resin selected from adsorbent non-ionic resins.

In another more preferred embodiment, the acid activated anion exchange resin is a weakly basic anion exchange resin, and the adsorbent non-ionic resin is a macroreticular cross-linked aromatic polymer.

The anion exchange resins used as a chromatographic resin for the purification of hydroxytyrosol of the present invention are not particularly limited so long as they can be acid activated. Examples of preferred weakly basic anion exchange resins include polyamine-type resins (including polyamine-type chelating resins) such as reaction products of a styrene/divinylbenzene copolymer and diethylenetriamine or other, and resins as polymerization products of compounds mainly comprising allylamine, vinylamine or other; and acrylic resins such as copolymers of divinylbenzene and amide compounds which comprise acrylic acid or methacrylic acid and dimethylaminopropylamine or other. Other resins may also be used in which the aforementioned weakly basic anion exchange resin is partly substituted with strongly basic exchange groups such as trimethylamine, dimethylethanolamine or other. More specifically, known in the art resins which have been used so far can be used, for example, Diaion WA10, WA20, WA21 and WA30 (Mitsubishi Chemical), Amberlite IRA-35, IRA-67 (IRA-68), IRA-93ZU, IRA-94S, IRA-478 (Rhom & Haas), WGR-2 (Dow Chemical) and other.

According to the invention process, these resins are acid activated before being used, preferably with acetic acid. These resins are particularly suitable for the invention process in view of their low cost and of the fact that they can be regenerated in mild conditions. Additionally, the weakly basic nature of the resin allows the partial separation of hydroxytyrosol and tyrosol molecules. From the comparison of the peak ratio hydroxytyrosol/tyrosol and the HPLC purity of the hydroxytyrosol peak of FIGS. 2 and 3, it can be appreciated the efficiency of the chromatographic separation according to the invention.

In fact, the use of a weakly anionic exchange resin allows to separate very similar compounds during the elution, this is not possible by the prior art techniques using strong anionic exchange resins, because the elution of such resins is generally an all-or-nothing process. As previously mentioned, a further advantage is that the retained products can be eluted with water, without using any polar solvent such as methanol.

Suitable adsorption resins are based on non-ionic, hydrophobic, macroreticular cross-linked aromatic polymer. Such resins are typically aromatic polymers, such as styrene and divinylbenzene copolymers, which may be cross-linked. Such resins are known and are generally prepared by polymerization of the appropriate monomers. The adsorption resins used as a chromatographic resin for the purification of hydroxytyrosol of the present invention are not particularly limited so long as they can be water eluted. Examples of preferred adsorption resins include: Amberlite® XAD-4, XAD-7, XAD-1180, XAD-16 and XAD-1600 (available from Rohm & Haas); XUS-40323.00, XUS-40285.00 and XUS-40283.00 (available from Dow Chemical Co.); and SP-700, SP-825, SP850, Diaion HP 10, HP 20, HP 30, HP 40 and HP 50 (available from Mitsubishi Chemical).

These type of resins are particularly suitable for the invention process in view of their very high adsorption capacity for hydroxytyrosol and of the fact that, thanks to the low content of by-products in the solution obtained after hydrolysis, the adsorbed hydroxytyrosol can be recovered by elution with water, only, without any polar solvent such as methanol or ethanol, as was instead required by the prior art techniques. Adsorbed hydroxytyrosol is recovered substantially quantitatively.

In the shown preferred embodiment, the process of the invention provides for a two-step purification on chromatographic columns.

Liquid A, as obtained from the initial steps a) and b), i.e. hydrolysis and solid separation, is charged into column 11, containing the anion exchange resin 12 as above detailed. The permeate is sent to waste treatment (not shown). Demineralized water from water supply 13 is then fed to column 11 to elute the retained products and the eluted liquid is collected in reservoir 14. The thus obtained liquid product (liquid B) has a purity in hydroxytyrosol of at least 75%, and generally of at least 80%, the purity being determined as the % of the peak areas in a chromatogram by HPLC at 280 nm. The recovery of retained hydroxytyrosol from the resin is at least 85% and is generally at least 90%.

FIG. 3 shows the relevant HPLC chromatogram of the obtained purified liquid product B.

In the second purification step, liquid product B is charged into column 15, containing a non-ionic adsorption resin 16, as above detailed. The permeate is sent to waste treatment and the adsorbed hydroxytyrosol is recovered by elution with demineralized water from supply 13 and is collected in reservoir 17.

Liquid C, i.e. the liquid collected in reservoir 17 has a purity in hydroxytyrosol of at least 90%, and generally of at least 95%, the purity being determined as the percent of the peak areas in a chromatogram by HPLC at 280 nm. The recovery of retained hydroxytyrosol from the resin is at least 90% and is generally at least 95% and substantially quantitative. FIG. 4 shows the relevant HPLC chromatogram of the obtained purified liquid product C.

FIG. 1 also shows a source of acetic acid 18 that is connected to column 11 for acid activation of resin 12 and a source of NaOH 19 or other suitable base for regeneration of the same. Additionally, a source of NaOH 19 for regeneration of resin 16 is connected to column 15 and a source of sulphuric acid 21 for resin surface activation is also shown.

As for liquid A, also liquid B and liquid C can be concentrated in concentration means 10, e.g. by evaporation or TFF, preferably by reverse osmosis; concentration is preferably carried out on liquids B and C, preferably liquid C, to a hydroxytyrosol content that is easily up to 10%, and that can reach 20%, 35% and even 40% by weight of hydroxytyrosol in the concentrated liquid product (i.e. extract).

In a further step of the invention process, the liquid products obtained by the previously discussed steps are dried in dryer means 20, e.g. freeze-dryer, vacuum rotoevaporator or preferably by spray-dryer, to produce a solid final product. The final product characteristics will be different according to the starting product (A, B or C) that is dried, the purity of the dry product being within the range of 45% to 99% (HPLC at 280 nm).

This drying step is preferably carried out on liquid products B and C, after concentrating them as above disclosed. The drying step can advantageously make use of carriers suitable for the final use of the dry product; suitable carriers are e.g. maltodextrines, lactose, lecithins, caseinates etcetera.

Suitable drying techniques are known in the art and comprise spray drying (usually with the use of carriers), freeze-drying and water evaporation under vacuum. The resulting products will have a hydroxytyrosol content of 0.5% to 10% and up to 20% (w/w) if a carrier is used, the hydroxytyrosol content can reach up to about 95% (w/w) if no carrier is used. It should be noticed that the invention process provides a purified liquid product (B and especially C) that is so pure that it can be evaporated to a dry powder even without carriers, this being not possible with known techniques.

The extracts of the invention are suitable to prepare oral composition comprising olive polyphenols in an amount effective to provide in a daily serving at least 5 mg of hydroxytyrosol and its derivatives (e.g. oleuropein complex and tyrosol) wherein said olive polyphenols comprises a weight ratio of hydroxytyrosol to aldehydic form of oleuropein aglycone of between 5:1 and 850:1.

The oral composition of the invention is comprising olive polyphenols in an amount effective to provide in a daily serving at least 5 mg of hydroxytyrosol and its derivatives (e.g. oleuropein complex and tyrosol) wherein said olive polyphenols comprises a weight ratio of hydroxytyrosol to oleuropein greater than 200:1.

The invention will now be further disclosed with reference to the following non-limiting examples.

Example 1

Hydroxytyrosol Extraction from Olive Waste (Orujillo), Purification of the Water Phase 250 g of a sample of dry olive waste, orujillo, are mixed with 838 ml of demineralized water and 16.7 g of sulphuric acid (98%). The obtained mixture is kept in autoclave for 30 minutes at 121° C. After that, the aqueous phase is separated from the solid residue, by filtering on a filter. The solid phase, retained on the filter, is washed with 310 ml of demineralized water, and the water coming from this washing operation is collected with the aqueous phase previously recovered. The aqueous phase, approximately 860 ml, is then centrifuge refined to eliminate solid particles passed through the filter. After solid elimination, 835 ml of crude aqueous extract, containing 1.41 g of hydroxytyrosol, with a HPLC purity of 47.5%, are obtained.

Example 2

Ion Exchange Hydroxytyrosol Purification

A sample of 835 ml of crude aqueous extract containing 1.41 g of hydroxytyrosol obtained according to Example 1, is loaded on a column containing a ion exchange resin of the anionic type, previously activated by means of acetate cycle. For example, Diaion WA10 may be used. The liquid phase recovered at the end of the column, does not contain any hydroxytyrosol, which is instead continuously eluted with demineralized water until at least 90% of the initially charged hydroxytyrosol is recovered. The eluted phase contains approximately 1.27 g of hydroxytyrosol with an HPLC purity of about 80.85%.

Example 3

Ion Exchange and Adsorption Hydroxytyrosol Purification

A sample of 835 ml of crude aqueous extract containing 1.41 g of hydroxytyrosol obtained according to Example 1, is loaded on a column containing an ion exchange resin of the anionic type, previously activated by means of acetate cycle. For example, IRA-67 may be used. The liquid phase recovered at the end of the column, does not contain any hydroxytyrosol, which is instead continuously eluted with demineralized water until at least 90% of the initially charged hydroxytyrosol is recovered.

The eluted phase coming from the first column, is charged on a column containing an adsorption resin. For example, resin XAD-1180 may be used. The liquid phase recovered at the end of the column, does not contain any hydroxytyrosol. Then, hydroxytyrosol is eluted from the resin with demineralized water until at least 90% of the initially charged hydroxytyrosol is recovered.

The eluted phase contains approximately 1.14 g of hydroxytyrosol with an HPLC purity of about 95.72%.

Example 4

Concentration of Hydroxytyrosol Crude Extract Enriched by Evaporation

The aqueous phase obtained in Example 1 before the centrifugation step, approximately 860 ml, is concentrated by evaporation in order to reach a final volume of about 193 ml. The aqueous phase is then centrifuge refined to eliminate solid particles passed through the filter. After solid elimination, 160 ml of crude aqueous extract, containing 1.41 g of hydroxytyrosol, with a HPLC purity of 47.5%, are obtained.

Example 5

Concentration of Hydroxytyrosol Ion Exchange Purified Extract Enriched by Reverse Osmosis A sample of 80 l of crude aqueous extract containing 150 g of hydroxytyrosol obtained in a pilot plant according to Example 2, is concentrated using a reverse osmosis pilot plant, equipped with a 2.5 $m^2$ polymeric membrane, in order to reduce the volume to 10 l of concentrate product. A 0.3 $m^2$ membrane made of the same material is then used in order to obtain a hydroxytyrosol concentrate containing 10.8% of hydroxytyrosol with an HPLC purity of 80.53%.

Example 6

Concentration of Hydroxytyrosol Ion Exchange and Adsorption Purified Extract by Reverse Osmosis A sample of 546 l of crude aqueous extract containing 135 g of hydroxytyrosol obtained in a pilot plant according to Example 3, is concentrated using a reverse osmosis pilot plant, equipped with a 2.5 $m^2$ polymeric membrane, in order to reduce the volume to 10 l of concentrate product. A 0.3 $m^2$ membrane made of the same material is then used, in order to obtain a hydroxytyrosol concentrate containing 12.20% of hydroxytyrosol with an HPLC purity of 95.27%.

Example 7

Spray-Drying of the Crude Extract Enriched in Hydroxytyrosol without any Purification A sample of 442 ml of crude aqueous extract containing 1.02 g of hydroxytyrosol obtained according to Example 1, is mixed with 100 g of maltodextrin, until maltodextrin was completely dissolved. For example, equivalent 10 dextrose potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 95 g of a brown powder, with a moisture of 6.85% (Karl Fischer) and a hydroxytyrosol richness of 0.98%, are obtained.

Example 8

Spray-Drying of the Partially Purified Aqueous Extract Enriched in Hydroxytyrosol A sample of 290 ml of aqueous extract containing 0.38 g of hydroxytyrosol obtained according to Example 2 and subsequently concentrated by reverse osmosis is mixed with 50 g of maltodextrin until maltodextrin was completely dissolved. For example, equivalent 10 dextrose potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 48.25 g of a greyish powder, with a moisture of 6.72% (Karl Fischer) and a hydroxytyrosol richness of 0.71%, are obtained.

Example 9

Spray-Drying of the Purified Aqueous Extract Enriched in Hydroxytyrosol

A sample of 188 ml of purified aqueous extract containing 0.29 g of hydroxytyrosol obtained according to Example 3, and subsequently concentrated by reverse osmosis, is slowly stirred with 28.5 g of maltodextrin. For example, equivalent 10 dextrose potato maltodextrin may be used. A peristaltic pump is used to feed the spray-dryer, which is previously equilibrated with an inlet air temperature of 175° C. The feeding speed is adjusted in order to obtain an outlet air temperature which is less than 100° C. 27.1 g of a white powder, with a moisture of 5.45% (Karl Fischer) and a hydroxytyrosol richness of 0.97%, are obtained.

Example 10

Preparation of a Highly Rich Hydroxytyrosol Powder

A sample of 1750 l of aqueous extract containing 432 g of hydroxytyrosol obtained, according to Example 3, in a pilot plant is concentrated according to Example 6, to obtain a hydroxytyrosol concentrate containing 39.04% of hydroxytyrosol with an HPLC purity of 95.60%. The concentrated solution is used to feed the spray-dryer, which is previously equilibrated with an inlet air temperature of 150° C. The feeding speed is adjusted in order to obtain an outlet air temperature less than 100° C. 375.84 g of a light brown powder, with a moisture of 4.35% (Karl Fischer) and a hydroxytyrosol richness of 94.74%, are obtained.

Example 11

Olive Extracts Production from Olives Fruits

25 Kg of a sample of olives fruits are mixed with 50 L of demineralized water. The obtained mixture is blended for a few minutes, and then 636 g of sulphuric acid (98%) were added. The obtained mixture is kept in autoclave for 30 minutes at 121° C. After that, the aqueous phase is separated from the solid olive residue, by filtering on a filter. The solid phase, retained on the filter, is washed with 12.5 L of demineralized water, and the water coming from this washing operation is collected with the aqueous phase previously recovered. The aqueous phase, approximately 63 L, is then filtered trough a Kieselguhr filter pre-coated with a Celite™ 500 diatomaceous earth to eliminate the extracted oil. The oil-free aqueous phase, about 56 L, is then centrifuge refined to eliminate solid particles passed through the Kieselguhr filter After solid elimination, 52 L of crude aqueous extract, containing 141 g of hydroxytyrosol, with a HPLC purity of 50.5%, are obtained.

Then, crude aqueous extract, is loaded on a column containing an ion exchange resin of the anionic type, previously activated by means of acetate cycle. For example, IRA-67 may be used. The liquid phase recovered at the end of the column, does not contain any hydroxytyrosol, which is instead continuously eluted with demineralized water until at least 90% of the initially charged hydroxytyrosol is recovered.

The eluted phase coming from the first column is charged on a column containing an adsorption resin. For example, resin XAD-1180 may be used. The liquid phase recovered at the end of the column, does not contain any hydroxytyrosol. Then, hydroxytyrosol is eluted from the resin with demineralized water until at least 90% of the initially charged hydroxytyrosol is recovered.

The eluted phase contains approximately 114 g of hydroxytyrosol with an HPLC purity of about 96.7%.

Then, a 461 L fraction of purified extract containing 114 g of hydroxytyrosol obtained in a pilot plant is concentrated using a reverse osmosis pilot plant, equipped with a 2.5 $m^2$ polymeric membrane, in order to reduce the volume to 10 l of concentrate product. A 0.35 $m^2$ membrane made of the same material is then used, in order to obtain a hydroxytyrosol concentrate containing 3.5% of hydroxytyrosol. Finally the RO concentrate is rotaevaporated at 78° C. under a vacuum pressure of 245 mbar to allow about 10 times concentration of the olive fruit extract in liquid form reaching a final concentration of 37.2% (w/w) with an HPLC purity of 93.3%.

Example 12

Preparation of Olive Fruit Extract Powder by Spray-Drying

A sample of 260 ml of purified olive extract in liquid form containing 19.5 g of hydroxytyrosol obtained according to Example 11, is slowly stirred with 58 g of maltodextrin previously dissolved in 260 ml of demineralized water. For example, potato maltodextrin may be used. A peristaltic pump is used to feed the spray-dryer, which is previously equilibrated with an inlet air temperature of 150° C. The feeding speed is adjusted in order to obtain an outlet air temperature which is less than 100° C. 76 g of a white powder, with a moisture of 5.4% (Karl Fischer) and a hydroxytyrosol richness of 21.9% (w/w), are obtained.

Example 13

Hydroxytyrosol Extraction from Three Phases Pomaces (Defatted Orujo), Purification of the Aqueous Phase 475.5 g of a sample of three phases pomace with a humidity of 60.55%, are mixed with 800 ml of demineralized water and 26.36 g of sulphuric acid (98%). The obtained mixture is kept in autoclave for 30 minutes at 121° C. After that, the aqueous phase is separated from the solid residue, by filtering on a 600 micron polypropylene filter. The filtered aqueous phase, approximately 795 ml, is concentrated by evaporation in order to reach a final volume of about 343.8 ml. The aqueous phase is then centrifuge refined to eliminate solid particles passed through the filter. After solids elimination, 275 ml of crude aqueous extract, containing 0.97 g of hydroxytyrosol, with a HPLC purity of 54%, are obtained.

Example 14

Ion Exchange and Adsorption Purification of Hydroxytyrosol Deriving from Three Phases Pomace (Defatted Orujo)

A sample of 275 ml of crude aqueous extract containing 0.97 g of hydroxytyrosol obtained according to Example 13, is loaded on a column containing an ion exchange resin of the anionic kind, previously activated by means of acetate cycle. For example, Diaion WA10 resin may be used. The liquid phase recovered at the end of the column, does not contain any hydroxytyrosol, which is instead continuously eluted with demineralized water until at least 90% of the initially charged hydroxytyrosol is recovered.

The eluted phase coming from the first column is loaded on a column containing an adsorption resin. For example, resin Diaion HP20 may be used. The liquid phase recovered at the end of the column, does not contain any hydroxytyrosol. Then, hydroxytyrosol is eluted from the resin with demineralized water until at least 90% of the initially charged hydroxytyrosol is recovered.

The eluted phase contains approximately 0.80 g of hydroxytyrosol with an HPLC purity which is higher than 95%.

As previously mentioned, the process of the invention provides for preparing an extract containing hydroxytyrosol starting from olives and/or pomaces without making use of organic polar solvents. The products obtained according to this process, both the final products and the intermediate products, are therefore free from organic polar solvents. The products are also substantially free from sugars and salts. This is possible by the combined use of the claimed hydrolysis conditions and purification procedure.

The final product, because of its high purity and high hydroxytyrosol content, in particular a solid hydroxytyrosol extract free from carriers and organic solvents is highly suitable for use in the food industry, and in cosmetic and pharmaceutical industries.

Figure 5:
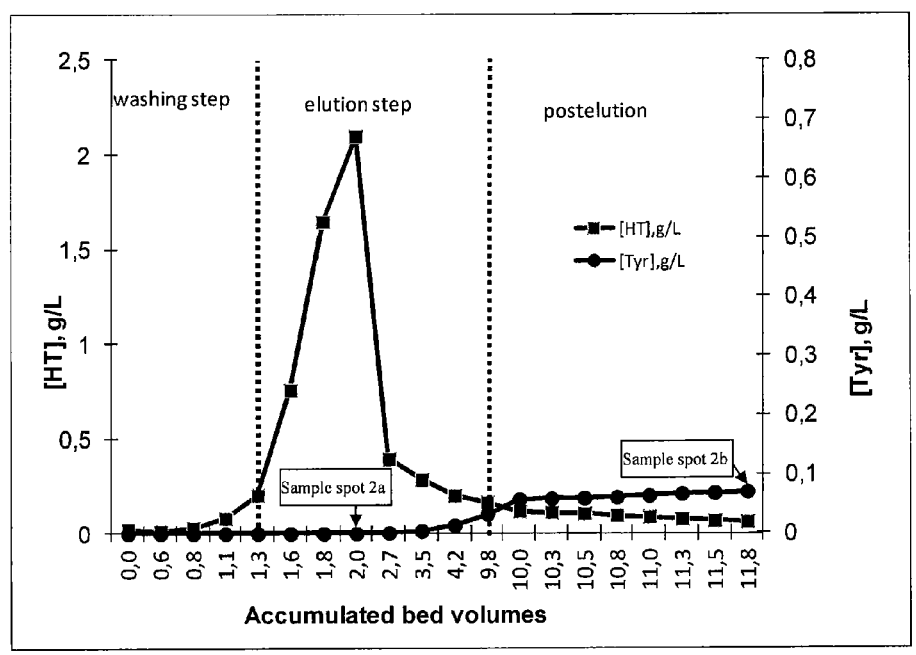
FIG. 5 is a chromatographic profile showing the separation of hydroxytyrosol and tyrosol peaks in adsorption column eluted with water. Also 2 marks are signaling the bed volumes at which sample spot 2a and sample spot 2b were taken.
Figure 6A:
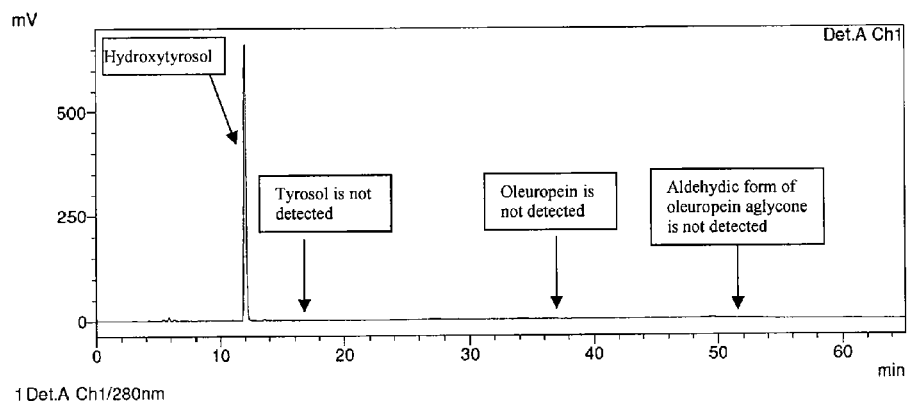
FIG. 6a is a HPLC chromatogram of the sample spot 2a (punctual sample at 2 BV) taken during collection of eluate fraction showing a complete separation of hydroxytyrosol and tyrosol in adsorption column eluted with water.
Figure 6B:
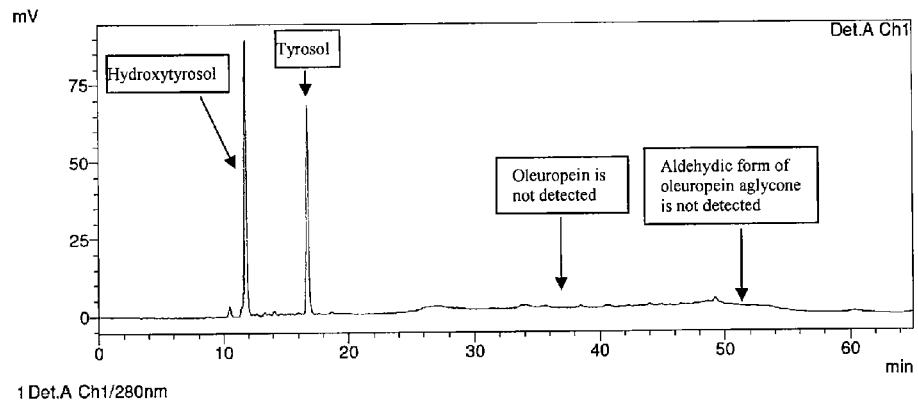
FIG. 6b is a HPLC chromatogram of the sample spot 2b taken (punctual sample at 11.8 BV), showing impurification of hydroxytyrosol with tyrosol that is eluted later than hydroxytyrosol in adsorption column eluted with water.

FIG. 5 is a chromatographic profile showing the separation of hydroxytyrosol and tyrosol peaks in adsorption column eluted with water. Also 2 marks are signaling the bed volumes at which sample spot 2a and sample spot 2b were taken. FIG. 6a is a HPLC chromatogram of the sample spot 2a (punctual sample at 2 BV) taken during collection of eluate fraction showing a complete separation of hydroxytyrosol and tyrosol in adsorption column eluted with water. FIG. 6b is a HPLC chromatogram of the sample spot 2b taken (punctual sample at 11.8 BV), showing contamination of hydroxytyrosol with tyrosol that is eluted later than hydroxytyrosol in adsorption column eluted with water.

Collection of eluate fraction is preferably completed after 9.8 BV avoiding ratios of hydroxyrtyrosol/Tyrosol lower than 55.

Example 15

Olive Extracts Production from Orujillo

2367 Kg of orujillo are loaded with 10250 L of demineralized water into a stirred glass lined reactor at atmospheric pressure. The obtained mixture is stirred for a few minutes, and then sulphuric acid (98%) was added to adjust to pH 1.50. The obtained mixture is kept stirred into a glass lined reactor 4 hours at 70° C. After that, NaOH (50%) was added to the reactor to adjust to pH 2.5±0.5, and then, the aqueous phase is separated from the solid olive residue, by using a centrifugal decanter. The solid phase was sent to waste handling. The aqueous phase, approximately 7900 L, is then centrifuge refined to eliminate the small solid particles passed through the centrifugal decanter step. After solid elimination, 7500 L of crude aqueous extract, containing 9.55 Kg of hydroxytyrosol, with a HPLC purity of 52.7%, were obtained; the weight ratios hydroxytyrosol/hydroxymethylfurfural (w/w), hydroxytyrosol/oleuropein and hydroxytyrosol/aldehydic form of oleuropein aglycone were found to be the values of 82, 289 and 8 respectively. A sample of crude aqueous extract was dried till moisture content lower than 10%, and then the content in PAHs was analyzed. The following data are the results:

benzo[a]pyrene<2 microg/Kg (quantification limit: 2 microg/Kg)
benzo(b)fluorantene<10 microg/Kg (quantification limit: 10 microg/Kg)
benzo(k)fluorantene<10 microg/Kg (quantification limit: 10 microg/Kg)
Benzo[g,h,i]perylene<10 microg/Kg (quantification limit: 10 microg/Kg)
indene(1,2,3-cd)pyrene<10 microg/Kg (quantification limit: 10 microg/Kg)

Then, the crude aqueous extract is loaded on a column containing an ion exchange resin of the anionic type, previously activated by means of citrate cycle. For example, IRA-67 may be used. The liquid phase recovered at the end of the column, does not contain any hydroxytyrosol, which is instead continuously eluted with demineralized water until at least 90% of the initially charged hydroxytyrosol is recovered.

The eluted phase coming from the first column is concentrated by reverse osmosis till a final volume equivalent to 1.8 bed volumes of the adsorption resin contained at the second column. The reverse osmosis concentrate is charged at the second column containing an adsorption resin. For example, 1000 L resin XAD-1180 may be used, then the loaded reverse osmosis concentrate is 1800 L (1.8 bed volumes). The liquid phase recovered at the end of the column after complete the loading phase of reverse osmosis concentrate (column permeate fraction), does not contain any hydroxytyrosol. After that, resin is washed with 1.33 bed volumes of water. Then the water elution phase starts, and the column eluate fraction is collected into the purified product tank. Hydroxytyrosol is eluted from the resin with 8.45 bed volumes of demineralized water (same quality that the one used for the washing step) until the HPLC analysis of a spot sample of the eluate take at outlet of the column presents a ratio hydroxytyrosol/tyrosol (w/w) lower than 15/1. The chromatographic profile showing the separation of hydroxytyrosol and tyrosol peaks is presented in FIG. 5. Presence of oleuropein and aldehydic form of oleuropein aglycone is checked by HPLC but these compounds are not detectable at any moment during the elution step, being the detection limits for both compounds 500 ppm.

The eluted phase contains approximately 7400 g of hydroxytyrosol (at least 90% of the initially loaded hydroxytyrosol) with an HPLC purity of about 95.7% and a ratio hydroxytyrosol/tyrosol (w/w) of 113/1.

Then, the eluted fraction of purified extract containing 7400 g of hydroxytyrosol is concentrated by reverse osmosis, in order to reduce the volume to 230 L of concentrate product. Finally the RO concentrate is rotaevaporated at 78° C. under a vacuum pressure of 245 mbar to allow about 14 times concentration of the olive fruit extract in liquid form reaching a final hydroxytyrosol concentration of 41.5% (w/w) with an HPLC purity of 94.8% and a ratio hydroxytyrosol/tyrosol (w/w) of 110/1 (see FIG. 5) and a ratio hydroxytyrosol/hydroxymethylfurfural (w/w), of 9050 was obtained. Presence of oleuropein and aldehydic form of oleuropein aglycone is checked by HPLC at olive fruit extract in liquid form (final product) but these compounds are not detectable, being the detection limits for both compounds 500 ppm (see FIG. 6a, FIG. 6b and FIG. 7 for identification of hydroxytyrosol, tyrosol, oleuropein and aldehydic form of oleuropein aglycone, comparison of peak profile and retention time of every compound). As the hydroxytyrosol content (w/w) was 41.5% and the detection limits for oleuropein and aldehydic form of oleuropein aglycone, 500 ppm a theoretical weight ratio hydroxytyrosol/oleuropein and hydroxytyrosol/aldehydic form of oleuropein aglycone could be calculated, being the theoretical value higher than 830.

The oleuropein of FIG. 7 is initially present in a sample of olive leaf extract purchased from Naturex; it was hydrolysed with beta-glucosidase from almond (purchased at Sigma) during 1 h at 25° C. at pH 5.0 in 100 mM sodium phosphate buffer. It is shown for comparative reasons with FIGS. 6a and 6b, especially to identify the retention times of oleuropein and aldehydic form of oleuropein aglycone formed during the reaction The ion species detected in purified olive extract in liquid form having a hydroxytyrosol concentration of 41.5% (w/w) with an HPLC purity of 94.8% and a ratio hydroxytyrosol/tyrosol (w/w) of 110/1 obtained according to Example 15 on the HPLC-DAD-MS systems are shown in FIG. 9.

FIG. 10 shows a chromatogram DAD (280 nm); BPC (Base Peak Chromatogram) in negative (−) and positive (+) ionization mode, for purified olive extract in liquid form having a hydroxytyrosol concentration of 41.5% (w/w) with an HPLC purity of 94.8% and a ratio hydroxytyrosol/tyrosol (w/w) of 110/1 obtained according to Example 15 dissolved in MeOH 0.1% HCOOH 100 mg/ml.

Example 16

Analysis of Ratios Hydroxytyrosol/Hydroxymethylfurfural (w/w), Hydroxytyrosol/Tyrosol (w/w) in 17 Different Production Lots of Olive Extracts Production from Orujillo, and Analysis of Oleuropein and Aldehydic Form of Oleuropein Aglycone The process of production of olive extracts from orujillo described at example 15, was carried out for 17 different production lots. The extension of the washing step was maintained fix (1.3 to 1.5 bed volumes), but the extension of the elution step was tested in the range 7 to 10 bed volumes, as shorter the bed volumes used for elution as higher the ratio hydroxytyrosol/tyrosol (w/w) obtaining values for such ratio from 55/1 to 618/1 (FIG. 8a). For all the analyzed lots the recovery of initially charged hydroxytyrosol at the eluted fraction is at least 80%. Presence of oleuropein and aldehydic form of oleuropein aglycone is checked by HPLC for every batch but these compounds are not detectable at any moment during the elution step nor in the final product.

The ratio hydroxytyrosol/hydroxymethylfurfural (w/w) was calculated for the crude aqueous extract after centrifugation, but before column purification the values were in the range 45:1 to 136:1 (see FIG. 8b).

Example 17

Preparation of Olive Fruit Extract Powder by Spray-Drying

A sample of 16 Kg of purified olive extract in liquid form containing 6640 g of hydroxytyrosol obtained according to Example 15, is slowly stirred with 19 Kg of maltodextrin previously dissolved in 220 L of demineralized water. For example, potato maltodextrin may be used. The solution is pumped to feed the spray-dryer, which is previously equilibrated with an inlet air temperature of 150° C. The feeding speed is adjusted in order to obtain an outlet air temperature which is less than 78° C. A production lot of 26.2 Kg of a white powder, with a moisture of 3.4% (Karl Fischer) and a hydroxytyrosol content of 22.8% (w/w), and a ratio hydroxytyrosol/tyrosol (w/w) of 115/1 and a ratio hydroxytyrosol/hydroxymethylfurfural (w/w), of 9136 were obtained.

Example 18

HPLC-DAD-MS Characterization of Olive Fruit Extract

A sample of 500 g of purified olive extract in liquid form having a hydroxytyrosol concentration of 41.5% (w/w) with an HPLC purity of 94.8% and a ratio hydroxytyrosol/tyrosol (w/w) of 110/1 obtained according to Example 15 was used as test item with the aim of identifying described phenolic compounds (hydroxytyrosol, tyrosol, etc.) and the presence of impurities. HPLC-DAD-MS systems with two types of mass analyzers: TOF (Time of Flight) and IT (Ion Trap). The former provides the exact mass of a given molecule and with the aid of the external laboratory of analysis database a possible identity can be established. In addition, the identity of the target compound could be confirmed by MS" experiments provided by the Ion Trap. A specific search of oleuropein and aldehydic form of oleuropein aglycone has been carried out.

HPLC-DAD-TOF System

The chromatographic separation is performed on a rapid resolution C18 column 50×3.0 mm, 1.8 μm under gradient conditions. The mobile phase consists of a mixture of methanol and water, both containing 0.1% of formic acid, with the aim of promoting the ionization of the compounds in samples.

The signals are registered in a diode array detector (at 280 nm) and in a TOF mass spectrometer detector with an electrospray ion source (ESI).

HPLC-DAD-IT System

In addition, an ion trap mass analyzer has been used with the aim of elucidating and confirming the molecules structures, which has been previously identified in the RRLC-TOF system. For this purpose, a C18 column 150×2.1 mm, 3.5 μm is used under gradient conditions, because d the system cannot work at pressures above 400 bars. The rest of chromatographic conditions are the same as those described in the previous section.

The identified chromatographic peaks are compiled in FIG. 9 and the chromatographic profile and composition is presented in FIG. 10. There are only selected the ones that have a certain absorbance at 280 nm, because this is the specific wavelength for phenolic compounds.

FIG. 9 shows the results obtained with IT and TOF mass analyzers. In both cases, the ionization has been carried out in negative and positive polarity. Therefore, the ions obtained in each ionization mode are shown in the table attached to the ionic species detected.

Concerning to the phenolic compounds, the presence of hydroxytyrosol (peak 2) and tyrosol (peak 4) has been confirmed. The tyrosol molecule is not ionized in the operating conditions, and it has been identified by comparison of the retention time with a commercial standard. Oleuropein and aldehydic form of oleuropein aglycone, which are other phenolic compounds of interest, have not been detected in the analyzed olive extract.

Example 19

Preparation of a Dietary Supplement Having as Active Ingredient an Olive Fruit Extract A sample of 518 g of purified olive extract in form of white powder, with a moisture of 3.4% (Karl Fischer) and a hydroxytyrosol content of 22.8% (w/w), and a ratio hydroxytyrosol/tyrosol (w/w) of 115/1 obtained according to Example 16, was filled into a biconic mixer and after that 1978 g of potato maltodextrin, 52 g of magnesium esterate and 52 g of tri-calcium phosphate, total batch size 2600 g. After 15 minutes of mixing the powder has an improved flowability in comparison with the initial olive extract, allowing a very good filling of hard gelatine capsules of size 00, with a very accurate net weight of 0.294±0.012 g (see FIG. 11).

The capsules were automatically cleaned externally and filled into a blistering machine that produces the blisters with 30 capsules. Finally blisters were manually introduced into the final packing.

Example 20

Preparation of a Olive Oil Having as Active Ingredient an Olive Fruit Extract and Use of Such Oral Compositions for Contribute to the Protection of Blood Lipids from Oxidative Stress The objective of the study was to analyze the protection of blood lipids from oxidative stress due to the intake of the oral compositions of olive oil added with a hydroxytyrosol-rich olive extract in a human intervention study by measuring the serum levels of oxidized LDL.

The selection of participants in the pilot study has followed a series of criteria listed below:
Inclusion Criteria:
1. All participants must give their written informed consent after receiving oral and written information about the study
2. Aged between 18 and 65
3. Body mass index (BMI) between 18.5 and 30 kg/m$^2$
4. Healthy men (without known diseases, including hypertension, hypercholesterolemia, diabetes and psoriasis)
5. Not having used dietary supplements or having donated blood two months before the study and during its development
Exclusion Criteria:
1. Cardiovascular disease at the time of the study or before that
2. Diabetes mellitus or other serious chronic disease, including allergies and severe psoriasis at the time of the study or before that
3. Hypertension at the time of the study or before that
4. Knowledge or belief of alcohol, drugs or medication abuse All participants have the right to withdraw at any time without explanation. In addition, participants may be excluded from the intervention if failure to follow the study guidelines occurs.

There are no side effects expected in this study.

The number of participants in this study was that of 20, divided in two groups of 10 participants who consumed:
  Group 1: 25 ml extra virgin olive oil (without addition of olive extract, used as control) daily at a single dose.
  Group 2: 25 ml fortified extra virgin olive oil (with addition of an olive extract prepared according ex. 15, providing a dose of 5 mg of hydroxytyrosol and its derivatives (e.g. oleuropein complex and tyrosol) daily at a single dose.

The duration of the study was that of 4 weeks. Blood samples were taken in fasting at days 0, 14 and 28. Blood sampling was performed by Laboratorios Munuera S.L.

With the blood samples the measurement of oxidized LDL was performed:

The analysis of results showed a 35% decrease at the plasmatic level of oxidized LDL in the group 2 participants. Such difference at the level of oxidized LDL was determined as statistically significantive when compared with the control group, p<0.01 (Tukey's Test). The results of the intervention study are shown in the FIG. 12.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The invention claimed is:

1. A process for producing a food in the food industry, comprising adding an extract obtainable by extraction from a starting material selected from olives and/or pomaces, residues of olives after the extraction of olive oil, wherein said extract contains hydroxytyrosol and tyrosol, the amount of sugars per 100 g or 100 mL of extract is 0.5 g or less, the residual content of Benzo[a]pyrene in said extract is less than 2 microg/Kg (weight BaP/weight of extract as dry matter), containing a weight ratio of hydroxytyrosol to hydroxymethylfurfural of between 45:1 and 10000:1 and the content of hydroxytyrosol in said extract is at least 0.5% (w/w) and the hydroxytyrosol purity is at least 40% (by HPLC 280 nm) to said food.

2. A process for producing a cosmetic composition, comprising adding an extract obtainable by extraction from a starting material selected from olives and/or pomaces, residues of olives after the extraction of olive oil, wherein said extract contains hydroxytyrosol and tyrosol, the amount of sugars per 100 g or 100 mL of extract is 0.5 g or less, the residual content of Benzo[a]pyrene in said extract is less than 2 microg/Kg (weight BaP/weight of extract as dry matter), containing a weight ratio of hydroxytyrosol to hydroxymethylfurfural of between 45:1 and 10000:1 and the content of hydroxytyrosol in said extract is at least 0.5% (w/w) and the hydroxytyrosol purity is at least 40% (by HPLC 280 nm) to said cosmetic composition.

3. A process for producing a pharmaceutical composition, comprising adding an extract obtainable by extraction from a starting material selected from olives and/or pomaces, residues of olives after the extraction of olive oil, wherein said extract contains hydroxytyrosol and tyrosol, the amount of sugars per 100 g or 100 mL of extract is 0.5 g or less, the residual content of Benzo[a]pyrene in said extract is less than 2 microg/Kg (weight BaP/weight of extract as dry matter), containing a weight ratio of hydroxytyrosol to hydroxymethylfurfural of between 45:1 and 10000:1 and the content of hydroxytyrosol in said extract is at least 0.5% (w/w) and the hydroxytyrosol purity is at least 40% (by HPLC 280 nm) to said pharmaceutical composition.

4. A process for producing a food according to claim 1, wherein said extract is suitable to provide in a daily serving at least 5 mg of hydroxytyrosol and its derivatives.

5. A process according to claim 2, wherein said extract is a liquid extract and has a total phenol content of at least 35% (w/w), an hydroxytyrosol content of at least 35% (w/w) and a purity of at least 90% (by HPLC 280 nm).

6. A process according to claim 5, wherein the content of hydroxytyrosol of said extract is at least 45% (w/w).

7. A process according to claim 2, wherein said extract is a solid, has a total phenols content of at least 20% (w/w), the content of hydroxytyrosol in said extract is at least 20% (w/w) and the hydroxytyrosol purity is at least 90% (by HPLC 280 nm).

8. A process according to claim 7, wherein said extract has a hydroxytyrosol content of at least 90% (w/w) a purity of at least 90% and a total phenols content of at least 92% (w/w).

9. A process according to claim 8, wherein said extract is free from carriers.

10. A process according to claim 2, wherein the weight ratio of hydroxytyrosol:oleuropein in the extract is greater than 200:1.

11. A process according to claim 2, wherein the weight ratio of hydroxytyrosol:aldehydic form of oleuropein aglycone in the extract is between 5:1 and 850:1.

12. A process according to claim 2, wherein said extract is free from oleuropein and aldehydic form of oleuropein aglycone (by HPLC 280 nm).

13. A process according to claim 2, wherein the weight ratio of hydroxytyrosol:tyrosol in the extract is greater than 55:1.

14. A process according to claim 2, wherein the weight ratio of hydroxytyrosol:tyrosol in the extract is within the range of 55:1 to 618:1.

15. A process according to claim 2, wherein said extract is free from organic polar solvents.

16. A process according to claim 3, wherein said extract is a liquid extract and has a total phenol content of at least 35% (w/w), an hydroxytyrosol content of at least 35% (w/w) and a purity of at least 90% (by HPLC 280 nm).

17. A process according to claim 16, wherein the content of hydroxytyrosol of said extract is at least 45% (w/w).

18. A process according to claim 2, wherein said extract is a solid, has a total phenols content of at least 20% (w/w), the content of hydroxytyrosol in said extract is at least 20% (w/w) and the hydroxytyrosol purity is at least 90% (by HPLC 280 nm).

19. A process according to claim 18, wherein said extract has a hydroxytyrosol content of at least 90% (w/w) a purity of at least 90% and a total phenols content of at least 92% (w/w).

20. A process according to claim 19, wherein said extract is free from carriers.

21. A process according to claim 3, wherein the weight ratio of hydroxytyrosol:oleuropein in the extract is greater than 200:1.

22. A process according to claim 3, wherein the weight ratio of hydroxytyrosol:aldehydic form of oleuropein aglycone in the extract is between 5:1 and 850:1.

23. A process according to claim 3, wherein said extract is free from oleuropein and aldehydic form of oleuropein aglycone (by HPLC 280 nm).

24. A process according to claim 3, wherein the weight ratio of hydroxytyrosol:tyrosol in the extract is greater than 55:1.

25. A process according to claim 3, wherein the weight ratio of hydroxytyrosol:tyrosol in the extract is within the range of 55:1 to 618:1.

26. A process according to claim 3, wherein said extract is free from organic polar solvents.

* * * * *